US008268296B2

(12) United States Patent
Knappe et al.

(10) Patent No.: US 8,268,296 B2
(45) Date of Patent: Sep. 18, 2012

(54) COSMETIC COMPOSITION

(75) Inventors: Thorsten Knappe, Schenefeld (DE); René Scheffler, Ellerau (DE); Helen Walter, Hamburg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 454 days.

(21) Appl. No.: 12/447,265

(22) PCT Filed: Oct. 18, 2007

(86) PCT No.: PCT/EP2007/061129
§ 371 (c)(1),
(2), (4) Date: Apr. 27, 2009

(87) PCT Pub. No.: WO2008/052886
PCT Pub. Date: May 8, 2008

(65) Prior Publication Data
US 2010/0028272 A1    Feb. 4, 2010

(30) Foreign Application Priority Data

Oct. 30, 2006   (DE) .......................... 10 2006 051 729

(51) Int. Cl.
*A61K 8/00* (2006.01)
*A61K 8/18* (2006.01)
*A61K 8/72* (2006.01)
*A61K 8/02* (2006.01)
*A61Q 5/12* (2006.01)
*A61Q 5/06* (2006.01)

(52) U.S. Cl. .................... 424/70.1; 424/401; 424/70.11; 424/70.12; 424/70.16

(58) Field of Classification Search .......................... None
See application file for complete search history.

(56) References Cited

U.S. PATENT DOCUMENTS

| 3,753,968 A | 8/1973 | Ward |
| 5,658,552 A * | 8/1997 | Bunning et al. ................ 424/45 |
| 5,773,595 A | 6/1998 | Weuthen et al. |
| 6,060,071 A | 5/2000 | Motitschke et al. |
| 6,235,696 B1 | 5/2001 | Hensen et al. |
| 6,235,913 B1 | 5/2001 | Raths et al. |
| 6,267,973 B1 | 7/2001 | Motitschke et al. |
| 6,300,297 B1 | 10/2001 | Seipel et al. |
| 6,300,508 B1 | 10/2001 | Raths et al. |
| 6,375,932 B1 | 4/2002 | Hiwatashi et al. |
| 6,403,112 B2 | 6/2002 | Motitschke et al. |
| 6,498,268 B1 | 12/2002 | Raths |
| 7,332,466 B2 | 2/2008 | Schmid et al. |
| 2004/0223933 A1 * | 11/2004 | Hiwatashi et al. ......... 424/70.11 |

FOREIGN PATENT DOCUMENTS

| DE | 3139438 A1 | 4/1983 |
| DE | 4413686 C2 | 10/1995 |
| DE | 19736906 A1 | 3/1999 |
| DE | 19738866 A1 | 3/1999 |
| DE | 19756454 C1 | 6/1999 |
| DE | 19839261 C1 | 5/2000 |
| DE | 10240757 A1 | 7/2003 |
| EP | 0671161 A1 | 12/1994 |
| EP | 0998908 A2 | 5/2000 |
| WO | WO-99/13827 A1 | 3/1999 |

OTHER PUBLICATIONS

International Cosmetic Ingredient Dictionary and Handbook, Seventh Edition, 1997, Contents of the vol. 1 of 3 and Contents of the vol. 2 of 3, Editors John A. Wenninger et al., Published by the Cosmetic, Toiletry, and Fragrance Association 1101 17th Street, NW., Suite 300, Washington, DC 20036-4702.

Roemp-Lexicon, Chemie, The 10th Edition, "H-L", p. 1764, Edited by Jurgen Falbe—Manfred Regitz, Georg Thieme Verlag Stuttgart, New York, 1997.

* cited by examiner

*Primary Examiner* — Abigail Fisher

(57) ABSTRACT

A cosmetic agent, in particular a styling agent, containing, in a cosmetically acceptable carrier, a) at least one copolymer A made of at least one monomer A1 selected from acrylic acid, methacrylic acid, acrylic acid alkyl esters, and methacrylic acid alkyl esters, and at least one amphoteric monomer A2 selected from (meth)acryloylalkylbetaines of formula (A2-I) and (meth)acryloylalkylamine oxides of formula (A2-II), such that in formula (A2-I) and in formula (A2-II), $R^1$ denotes H or $CH_3$, $R^2$ and $R^3$, mutually independently in each case, denote optionally branched $C_{1-10}$ alkyl, and n denotes an integer from 1 to 20, and b) at least one film-forming and/or setting amphoteric polymer B different from copolymer A; and use of the agents for the temporary deformation of hairs.

10 Claims, No Drawings

COSMETIC COMPOSITION

RELATED APPLICATIONS

This application is a national stage application under 35 U.S.C. §371 of PCT/EP2007/061129, filed Oct. 18, 2007, which claims benefit of German application 102006051729.6, filed Oct. 30, 2006.

The present invention relates to cosmetic agents containing a special combination of polymers, and to the use of those agents, in particular for the temporary deformation of keratinic fibers.

"Keratin-containing" fibers are understood in principle as all animal hairs, e.g. wool, horsehair, angora wool, furs, feathers, and products or textiles produced therefrom. By preference, however, the keratinic fibers are human hairs.

The use of polymers in a wide variety of cosmetic agents is very common. They are used in agents for skin treatment and in agents for hair treatment, in agents that are rinsed off or out again immediately after application (so-called rinse-off products), and also in agents that remain on the skin or hair (so-called leave-on agents). The polymers are used for a very wide variety of reasons, and specific properties of the polymers are exploited in each case. In agents for skin treatment, in shampoos, hair rinses, or hair therapies, the spotlight is often on the thickening or care-providing properties of polymers. In agents for the temporary deformation of keratinic fibers, also hereinafter called "styling agents," in addition to these properties, film-forming and/or setting effects are principally sought after. Polymers often also serve as adjuvants that improve, or are what make possible, the deposition and immobilization of other active substances and ingredients on the skin or hair. For example, the addition of suitable polymers to hair coloring agents allows the abrasion resistance and durability of the color to be enhanced.

As a rule, cosmetic agents contain individual polymers that are specially tailored to achieve a very specific effect. If different effects are to be achieved, the addition of multiple polymers is necessary. If too many different polymers are used, however, this can produce a number of disadvantages. Problems can arise with formulation, for example, perhaps because the polymers react with one another or with other constituents of the agent, and precipitation or breakdown occur. Certain polymers also tend to become so tenaciously deposited onto the skin, and in particular onto the hair, that they can no longer be completely removed with ordinary washing; this results in an undesirable buildup of the polymer, and thus ultimately in stress on the skin or hair.

A continuing need therefore exists for polymers, or suitable combinations of a few polymers, that simultaneously exhibit as many of the desired properties as possible.

In the case of styling agents, for example, the polymers used must impart the strongest possible hold to the treated hair. In addition to a high degree of hold, however, styling agents must meet a whole series of further requirements. These can be subdivided roughly into properties on the hair; properties of the particular formulation, e.g. properties of the foam, gel, or sprayed aerosol; and properties that relate to handling of the styling agent, particular importance being placed on the properties on the hair. Especially to be mentioned are humidity resistance, low tack, and a balanced conditioning effect. In addition, a styling agent should be universally usable for as many hair types as possible. If the styling agent is a gel or a paste, the polymers additionally need to possess thickening properties.

The object of the present invention was therefore to make available suitable polymer combinations that already impart optimized properties to cosmetic agents without the addition of further active substances. In particular, the polymer combinations are intended to exhibit thickening and simultaneously film-forming and/or setting properties. Styling agents containing the polymers are to exhibit a very high degree of hold with no need, in that context, to forego flexibility and good humidity resistance.

It has now been found, surprisingly, that this can be achieved by means of a combination of special amphoteric polymers.

A first subject of the present invention is therefore a cosmetic agent containing, in a cosmetically acceptable carrier
  (a) at least one copolymer A made of
    at least one monomer A1 selected from acrylic acid, methacrylic acid, acrylic acid alkyl esters, and methacrylic acid alkyl esters; and
    at least one amphoteric monomer A2 selected from (meth)acryloylalkylbetaines of formula A2-I

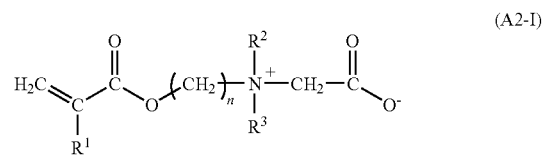

and (meth)acryloylalkylamine oxides of formula A2-II

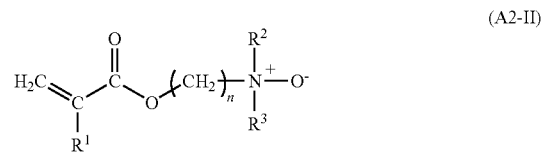

such that in formula A2-I and in formula A2-II
  $R^1$ denotes H or $CH_3$,
  $R^2$ and $R^3$, mutually independently in each case, denote optionally branched $C_{1-10}$ alkyl, and
  n denotes an integer from 1 to 20, and
(b) at least one film-forming and/or setting amphoteric polymer B different from copolymer A.

Film-forming and/or setting amphoteric polymers B are known. The same is true of copolymers A and their use as film-forming and/or setting polymers. It has now been shown, surprisingly, that a corresponding combination of the two polymer types possesses self-thickening properties, the outstanding film-forming and/or setting properties of the individual polymers being further enhanced. Styling agents containing a combination of these polymers are notable for a synergistic enhancement of the degree of hold, and good humidity resistance for the hold that is achieved.

As a first mandatory constituent, the cosmetic agents according to the present invention contain at least one copolymer A.

For purposes of the present invention, what are to be understood as "copolymers A" made of the aforesaid monomers are only those copolymers that contain, in addition to polymer units that result from the incorporation of the aforesaid monomers A1 and A2 into the copolymer, a maximum of 5 wt %, by preference a maximum of 1 wt %, of polymer units that are attributable to the incorporation of other monomers. By preference, copolymers A are constructed exclusively from polymer units that result from the incorporation of the aforesaid monomers A1 and A2 into the copolymer.

Preferred monomers A1 are acrylic acid, methacrylic acid, acrylic acid $C_{1-20}$ alkyl esters, and methacrylic acid $C_{1-20}$ alkyl esters.

Particularly preferably, monomer A1 is selected from acrylic acid, methacrylic acid, acrylic acid methyl ester, methacrylic acid methyl ester, acrylic acid ethyl ester, methacrylic acid ethyl ester, acrylic acid propyl ester, methacrylic acid propyl ester, acrylic acid isopropyl ester, methacrylic acid isopropyl ester, acrylic acid lauryl ester, methacrylic acid lauryl ester, acrylic acid cetyl ester, methacrylic acid cetyl ester, acrylic acid stearyl ester, and methacrylic acid stearyl ester, very particularly preferably from acrylic acid, methacrylic acid, acrylic acid methyl ester, methacrylic acid methyl ester, acrylic acid ethyl ester, methacrylic acid ethyl ester, acrylic acid lauryl ester, methacrylic acid lauryl ester, acrylic acid stearyl ester, and methacrylic acid stearyl ester.

Preferred monomers A2 are (meth)acryloylalkylbetaines of formula A2-I and (meth)acryloylalkylamine oxides of formula A2-II, $R^2$ and $R^3$ denoting, mutually independently in each case, methyl, ethyl, propyl, isopropyl, butyl, isobutyl, or tert.-butyl, particularly preferably methyl.

Preferred monomers A2 are furthermore selected from (meth)acryloylalkylbetaines of formula A2-I and (meth)acryloylalkylamine oxides of formula A2-II, n respectively denoting an integer from 1 to 5, by preference an integer from 1 to 3, and particularly preferably denoting 2.

Monomers A2 are preferably also selected from methacryloylalkylbetaines of formula A2-I and methacryloylalkylamine oxides of formula A2-II, $R^1$ respectively denoting $CH_3$.

Particularly preferably, monomers A2 are selected from methacryloylalkylbetaines of formula A2-I and methacryloylalkylamine oxides of formula A2-II, $R^2$ and $R^3$ denoting, mutually independently in each case, methyl, ethyl, propyl, isopropyl, butyl, isobutyl, or tert.-butyl, particularly preferably methyl, n denoting in each case an integer from 1 to 5, by preference an integer from 1 to 3, and particularly preferably 2, and $R^1$ respectively denoting $CH_3$.

Very particularly preferably, monomer A2 is selected from methacryloylalkylbetaines of formula A2-I and methacryloylalkylamine oxides of formula A2-II, $R^1$, $R^2$, and $R^3$ respectively denoting $CH_3$, and n denoting 2.

In a first preferred embodiment, the agent according to the present invention contains at least one copolymer A that is made of
  at least one monomer A1 selected from acrylic acid, methacrylic acid, acrylic acid methyl ester, methacrylic acid methyl ester, acrylic acid ethyl ester, methacrylic acid ethyl ester, acrylic acid propyl ester, methacrylic acid propyl ester, acrylic acid isopropyl ester, and methacrylic acid isopropyl ester, and
  methacryloylethylbetaine as monomer A2.

Corresponding copolymers are known, and are obtainable, for example, under the designations Diaformer Z-400, Diaformer Z-AT, Diaformer Z-301N, Diaformer Z-SM, and Diaformer Z-W of the Clariant company, and under the designations Yukaformer 202, Yukaformer 204, Yukaformer 206, and Yukaformer 301 of the Mitsubishi company; the use of Diaformer Z-301N is particularly preferred.

In a second preferred embodiment, the agent according to the present invention contains at least one copolymer A that is made of
  at least two monomers A1, the first monomer being selected from acrylic acid, methacrylic acid, acrylic acid methyl ester, methacrylic acid methyl ester, acrylic acid ethyl ester, methacrylic acid ethyl ester, acrylic acid propyl ester, methacrylic acid propyl ester, acrylic acid isopropyl ester, and methacrylic acid isopropyl ester, and the second monomer being selected from acrylic acid stearyl ester and methacrylic acid stearyl ester; and
  methacryloylethylamine oxide as monomer A2.

These copolymers, too, are known, and are obtainable under the designation Diaformer Z-632 of the Clariant company; the use of Diaformer Z-632 is particularly preferred.

In a third preferred embodiment, the agent according to the present invention contains at least one copolymer A that is made of
  at least three monomers A1, the first monomer being selected from acrylic acid, methacrylic acid, acrylic acid methyl ester, methacrylic acid methyl ester, acrylic acid ethyl ester, methacrylic acid ethyl ester, acrylic acid propyl ester, methacrylic acid propyl ester, acrylic acid isopropyl ester, and methacrylic acid isopropyl ester, the second monomer being selected from acrylic acid lauryl ester and methacrylic acid lauryl ester, and the third monomer being selected from acrylic acid stearyl ester and methacrylic acid stearyl ester; and
  methacryloylethylamine oxide as monomer A2.

Corresponding copolymers are likewise known, and are obtainable e.g. under the designations Diaformer Z-611, Diaformer Z-612, Diaformer Z-613, Diaformer Z-631, Diaformer Z-633, Diaformer Z-651, Diaformer Z-711N, Diaformer Z-712N, and Diaformer Z-731N of the Clariant company; the use of Diaformer Z-712N and Diaformer Z-651 is particularly preferred.

It is of course also possible for the agents according to the present invention to contain a mixture of at least two of copolymers A that are used in accordance with the three preferred embodiments just described.

The agents according to the present invention contain copolymer A by preference in a quantity from 0.01 to 20 wt %, particularly preferably 0.05 to 10 wt %, and very particularly preferably 0.1 to 5 wt %, based on the entire agent.

The agents according to the present invention can of course also contain multiple copolymers A, although the total quantity of copolymer A is by preference at most 20 wt %.

Copolymers A can be manufactured from the aforesaid monomers by means of known polymerization methods, and as a rule are commercially available.

As a second mandatory constituent) the agents according to the present invention for the temporary deformation of keratinic fibers contain at least one film-forming and/or setting amphoteric polymer B different from copolymer A.

The film-forming and/or setting amphoteric polymer B is selected by preference from the group of the copolymers made from monomers having carboxy and/or sulfone groups, in particular acrylic acid, methacrylic acid, itaconic acid, and monomers having amino groups, in particular monoalkylaminoalkyl acrylates, dialkylaminoalkyl acrylates, monoalkylaminoalkyl methacrylates, dialkylaminoalkyl methacrylates, monoalkylaminoalkyl acrylamides, dialkylaminoalkyl acrylamides, monoalkylaminoalkyl methacrylamides, dialkylaminoalkyl methacrylamides, and copolymers of N-octyl acrylamide, methyl methacrylate, hydroxypropyl methacrylate, N-tert.-butylaminoethyl methacrylate, and acrylic acid.

Particularly preferably, the agent according to the present invention contains as film-forming and/or setting amphoteric polymer B an N-octyl acrylamide/acrylic acid/tert.-butylaminoethyl methacrylate copolymer, particularly preferably the copolymer marketed by the National Starch company under the designation Amphomer® (INCI name: Octylacrylamide/Acrylates/Butylaminoethyl Methacrylate Copolymer).

The film-forming and/or setting amphoteric polymer B is contained by preference in a quantity from 0.01 to 20 wt %, by preference 0.1 to 15 wt %, particularly preferably 1.0 to 10 wt %, based on the entire agent. Several film-forming and/or setting amphoteric polymers B can of course also be contained, although the total quantity of film-forming and/or setting amphoteric polymers B is by preference at most 20 wt %.

In order to achieve the desired properties of the agent according to the present invention, the agent must contain both copolymer A and a film-forming and/or setting copolymer B different from copolymer A. The combination of very strong hold and outstanding humidity resistance that is desirable in particular for styling agents can thereby be obtained. It has been shown that an optimum properties profile is obtained when the agent contains copolymer A and the film-forming and/or setting amphoteric polymer B at a weight ratio from 1:20 to 20:1, by preference from 1:10 to 10:1, particularly preferably from 1:5 to 5:1, very particularly preferably 1:1 to 5:1. An excess of copolymer A improves the thickening properties of the polymer mixture.

In addition to copolymer A and film-forming and/or setting amphoteric polymers B, the agents can furthermore contain all further known film-forming and/or setting polymers. These film-forming and/or setting polymers can be both permanently and temporarily cationic, anionic, or nonionic.

Because polymers are often multifunctional, their functions cannot always be clearly and unequivocally distinguished from one another. This applies in particular to film-forming and setting polymers. It is explicitly stated at this juncture, however, that in the context of the present invention, both film-forming and setting polymers are essential. Because the two properties are also not entirely independent of one another, the term "setting polymers" is also always understood as "film-forming polymers," and vice versa.

Included among the preferred properties of the film-forming polymers is film formation. "Film-forming polymers" are to be understood as those polymers that, upon drying, leave behind a continuous film on the skin, hair, or nails. Film-formers of this kind can be used in a very wide variety of cosmetic products such as, for example, face masks, make-up, hair setting agents, hair sprays, hair gels, hair waxes, hair therapies, shampoos, or nail polishes. Particularly preferred are those polymers that possess sufficient solubility in alcohol or in water/alcohol mixtures to be present in completely dissolved form in the agent according to the present invention. The film-forming polymers can be of synthetic or natural origin.

"Film-forming polymers" are furthermore understood according to the present invention to be those polymers that, when used in a 0.01- to 20-wt % aqueous, alcoholic, or aqueous/alcoholic solution, are capable of depositing a transparent polymer film on the hair.

Suitable further synthetic film-forming, hair-setting polymers are, for example, homo- or copolymers that are constructed from at least one of the following monomers: vinylpyrrolidone, vinyl caprolactam, vinyl esters such as, for example, vinyl acetate, vinyl alcohol, acrylamide, methacrylamide, alkyl and dialkyl acrylamide, alkyl and dialkyl methacrylamide, alkyl acrylate, alkyl methacrylate, propylene glycol or ethylene glycol, the alkyl groups of these monomers being by preference $C_1$ to $C_7$ alkyl groups, particularly preferably $C_1$ to $C_3$ alkyl groups.

Mention may be made, by way of example, of homopolymers of vinylpyrrolidone or of N-vinylformamide. Further suitable synthetic film-forming, hair-setting polymers are, for example, copolymers of vinylpyrrolidone and vinyl acetate, terpolymers of vinylpyrrolidone, vinyl acetate, and vinyl propionate, polyacrylamides that are marketed, for example, under the commercial names Akypomine® P 191 of the CHEM-Y company, Emmerich, or Sepigel® 305 of the Seppic company; polyvinyl alcohols that are marketed, for example, under the commercial names Elvanol® of DuPont or Vinol® 523/540 of the Air Products company, and polyethylene glycol/polypropylene glycol copolymers that are marketed, for example, under the commercial names Ucon® of Union Carbide.

Suitable natural film-forming polymers are, for example, cellulose derivatives, for example hydroxypropyl cellulose having a molecular weight from 30,000 to 50,000 g/mol, which is marketed for example under the commercial name Nisso SI® by the Lehmann & Voss company, Hamburg.

Setting polymers contribute to the hold, and/or to building up the hair volume and hair fullness, of the overall hairstyle. These so-called setting polymers are at the same time also film-forming polymers, and are therefore generally typical substances for shaping hair-treatment agents such as hair setting agents, hair foams, hair waxes, hair sprays. It is certainly possible for film formation to be localized, and for only a few fibers to be connected to one another.

Substances that furthermore impart hydrophobic properties to the hair are preferred in this context, since they decrease the hair's tendency to absorb humidity, i.e. water. This decreases loose hanging of strands of hair, and thus ensures long-term hairstyle construction and retention. The so-called "curl retention" test is often used as a test method for this. These polymeric substances can furthermore be successfully incorporated into leave-in and rinse-off hair therapies or shampoos. Because polymers are often multifunctional, i.e. exhibit multiple effects that are desirable in terms of applications engineering, numerous polymers fall into multiple groups categorized in terms of effect; this is also the case in the CFTA handbook.

If the agents according to the present invention contain further film-forming and/or setting polymers, the latter are used by preference in a quantity from 0.01 to 20 wt %, by preference 0.1 to 15 wt %, based on the entire hair setting agent. Several film-forming and/or setting polymers can of course also be contained, although the total quantity of further film-forming and/or setting polymers is by preference at most 20 wt %.

In a preferred embodiment, the agents according to the present invention contain, as film-forming and/or setting polymers, exclusively copolymers A and film-forming and/or setting amphoteric polymers B.

The agents according to the present invention contain the polymers in a cosmetically acceptable carrier.

Preferred cosmetically acceptable carriers are aqueous, alcoholic, or aqueous/alcoholic media having by preference at least 10 wt % water, based on the entire agent. The alcohols contained can be, in particular, the lower alcohols having 1 to 4 carbon atoms usually used for cosmetic purposes, for example ethanol and isopropanol.

Organic solvents, or a mixture of solvents having a boiling point under 400° C., can be contained as additional co-solvents in a quantity from 0.1 to 15 weight percent, preferably 1 to 10 weight percent, based on the entire agent. Unbranched or branched hydrocarbons such as pentane, hexane, isopentane, and cyclic hydrocarbons such as cyclopentane and cyclohexane, are particularly suitable as additional co-solvents. Further particularly preferred water-soluble solvents are glycerol, ethylene glycol, and propylene glycol, in a quantity of up to 30 wt % based on the entire agent.

The agents preferably have a pH from 2 to 11. Particularly preferably, the pH range is between 2 and 8. Unless otherwise noted, the indications regarding pH refer in this context, for purposes of this document, to the pH at 25° C.

The agents according to the present invention can furthermore contain the adjuvants and additives that are usually added to the respective cosmetic agents.

Care-providing substances may be mentioned in particular as suitable adjuvants and additives. These are utilized in both skin and hair treatment agents, and with suitable selection of the care-providing substance can be incorporated, for example, into creams, shampoos, hair rinses, hair therapies, gels, pump and aerosol sprays, and foam products.

A silicone oil and/or a silicone gum can be used, for example, as a care-providing substance. In a particular embodiment of the invention, the agents contain at least one silicone oil and/or one silicone gum.

Silicones or silicone gums suitable according to the present invention are, in particular, dialkyl- and alkylarylsiloxanes such as, for example, dimethylpolysiloxane and methylphenylpolysiloxane, as well as their alkoxylated, quaternized, or even anionic derivatives. Cyclic and linear polydialkylsiloxanes, alkoxylated and/or aminated derivates thereof, dihydroxypolydimethylsiloxanes, and polyphenylsiloxanes are preferred.

Silicone oils produce a wide variety of effects. For example, they simultaneously influence dry and wet combability, the feel of the dry and wet hair, and shine. The skilled artisan understands the term "silicone oils" as several structures of organosilicon compounds. It is understood firstly as the dimethiconols (S1). These can be both linear and branched, and also cyclic or cyclic and branched. Linear dimethiconols can be represented by the following structural formula (S1-I):

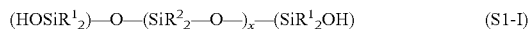

$$(HOSiR^1{}_2)-O-(SiR^2{}_2-O-)_x-(SiR^1{}_2OH) \quad (S1\text{-}I)$$

Branched dimethiconols can be represented by the structural formula (S1-II):

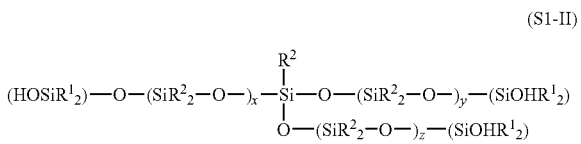

(S1-II)

The $R^1$ and $R^2$ radicals each denote, mutually independently, hydrogen, a methyl radical, a $C_2$ to $C_{30}$ linear, saturated or unsaturated hydrocarbon radical, a phenyl radical, and/or an aryl radical. Non-limiting examples of the radicals represented by $R^1$ and $R^2$ include alkyl radicals such as methyl, ethyl, propyl, isopropyl, butyl, isobutyl, pentyl, isopentyl, neopentyl, amyl, isoamyl, hexyl, isohexyl and the like; alkenyl radicals such as vinyl, halovinyl, alkylvinyl, allyl, haloallyl, alkylallyl; cycloalkyl radicals such as cyclobutyl, cyclopentyl, cyclohexyl, and the like; phenyl radicals, benzyl radicals, halogenated hydrocarbon radicals such as 3-chloropropyl, 4-bromobutyl, 3,3,3-trifluoropropyl, chlorocyclohexyl, bromophenyl, chlorophenyl, and the like, and sulfur-containing radicals such as mercaptoethyl, mercaptopropyl, mercaptohexyl, mercaptophenyl, and the like; by preference, $R^1$ and $R^2$ are an alkyl radical that contains 1 to approximately 6 carbon atoms, and particularly preferably $R^1$ and $R^2$ are methyl. The numbers x, y, and z are integers and range, mutually independently in each case, from 0 to 50,000. The molecular weights of the dimethiconols are between 1000 D and 10,000,000 D. The viscosities are between 100 and 10,000,000 cPs, measured at 25° C. using a glass capillary viscosimeter in accordance with Dow Corning Corporate Test Method CTM 0004 of Jul. 20, 1970. Preferred viscosities are between 1000 and 5,000,000 cPs; very particularly preferred viscosities are between 10,000 und 3,000,000 cPs. The most preferred range is between 50,000 und 2,000,000 cPs.

The following commercial products are recited as examples of such products: Botanisil NU-150M (Botanigenics), Dow Corning 1-1254 Fluid, Dow Corning 2-9023 Fluid, Dow Corning 2-9026 Fluid, Ultrapure Dimethiconol (Ultra Chemical), Unisil SF-R (Universal Preserve), X-21-5619 (Shin-Etsu Chemical Co.), Abil OSW 5 (Degussa Care Specialties), ACC DL-9430 Emulsion (Taylor Chemical Company), AEC Dimethiconol & Sodium Dodecylbenzenesulfonate (A & E Connock (Perfumery & Cosmetics) Ltd.), B C Dimethiconol Emulsion 95 (Basildon Chemical Company, Ltd.), Cosmetic Fluid 1401, Cosmetic Fluid 1403, Cosmetic Fluid 1501, Cosmetic Fluid 1401 DC (all the aforesaid Chemsil Silicones, Inc.), Dow Corning 1401 Fluid, Dow Corning 1403 Fluid, Dow Corning 1501 Fluid, Dow Corning 1784 HVF Emulsion, Dow Corning 9546 Silicone Elastomer Blend (all the aforesaid Dow Corning Corporation), Dub Gel SI 1400 (Stearinerie Dubois Fils), HVM 4852 Emulsion (Crompton Corporation), Jeesilc 6056 (Jeen International Corporation), Lubrasil, Lubrasil DS (both Guardian Laboratories), Nonychosine E, Nonychosine V (both Exsymol), San-Surf Petrolatum-25, Satin Finish (both Collaborative Laboratories, Inc.), Silatex-D30 (Cosmetic Ingredient Resources), Silsoft 148, Silsoft E-50, Silsoft E-623 (all the aforesaid Crompton Corporation), SM555, SM2725, SM2765, SM2785 (all the aforesaid GE Silicones), Taylor T-Sil CD-1, Taylor TME-4050E (all Taylor Chemical Company), TH V 148 (Crompton Corporation), Tixogel CYD-1429 (Sud-Chemie Performance Additives), Wacker-Belsil CM 1000, Wacker-Belsil CM 3092, Wacker-Belsil CM 5040, Wacker-Belsil DM 3096, Wacker-Belsil DM 3112 VP, Wacker-Belsil DM 8005 VP, Wacker-Belsil DM 60081 VP (all the aforesaid Wacker-Chemie GmbH).

Dimethicones (S2) constitute the second group of silicones that can be contained according to the present invention. They can be both linear and branched, and also cyclic or cyclic and branched. Linear dimethicones can be represented by the following structural formula (S2-I):

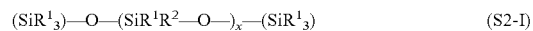

$$(SiR^1{}_3)-O-(SiR^1R^2-O-)_x-(SiR^1{}_3) \quad (S2\text{-}I)$$

Branched dimethicones can be represented by the structural formula (S2-II):

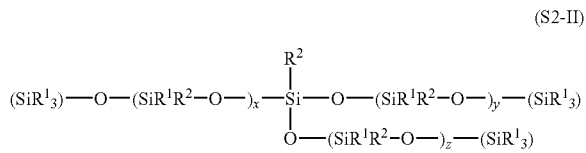

(S2-II)

The $R^1$ and $R^2$ radicals each denote, mutually independently, hydrogen, a methyl radical, a $C_2$ to $C_{30}$ linear, saturated or unsaturated hydrocarbon radical, a phenyl radical, and/or an aryl radical. Non-limiting examples of the radicals represented by $R^1$ and $R^2$ include alkyl radicals such as methyl, ethyl, propyl, isopropyl, butyl, isobutyl, pentyl, isopentyl, neopentyl, amyl, isoamyl, hexyl, isohexyl and the like; alkenyl radicals such as vinyl, halovinyl, alkylvinyl, allyl, haloallyl, alkylallyl; cycloalkyl radicals such as cyclobutyl, cyclopentyl, cyclohexyl, and the like; phenyl radicals, benzyl radicals, halogenated hydrocarbon radicals such as 3-chloropropyl, 4-bromobutyl, 3,3,3-trifluoropropyl, chlorocyclohexyl, bromophenyl, chlorophenyl, and the like, and sulfur-containing radicals such as mercaptoethyl, mercaptopropyl, mercaptohexyl, mercaptophenyl, and the like; by preference, $R^1$ and $R^2$ are an alkyl radical that contains 1 to approximately 6 carbon atoms, and particularly preferably $R^1$ and $R^2$ are methyl. The numbers x, y, and z are integers and range, mutually independently in each case, from 0 to 50,000. The molecular weights of the dimethicones are between 1000 D and 10,000,000 D. The viscosities are between 100 and 10,000,000 cPs, measured at 25° C. using a glass capillary viscosimeter in accordance with Dow Corning Corporate Test Method CTM 0004 of Jul. 20, 1970. Preferred viscosities are between 1000 and 5,000,000 cPs; particularly preferred viscosities are between 10,000 und 3,000,000 cPs. Very particularly preferably, the viscosity is in the range between 50,000 und 2,000,000 cPs.

Dimethicone copolyols (S3) constitute a further group of silicones that are suitable. Dimethicone copolyols can be represented by the following structural formulas:

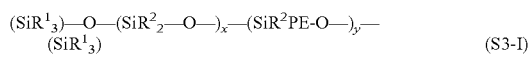

(S3-I)

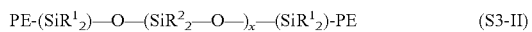

(S3-II)

Branched dimethicone copolyols can be represented by the structural formula (S3-III):

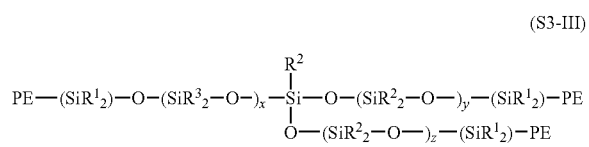

(S3-III)

or by the structural formula (S3-IV):

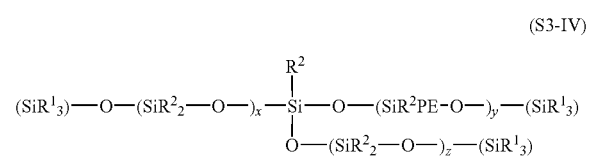

(S3-IV)

The $R^1$ and $R^2$ radicals each denote, mutually independently, hydrogen, a methyl radical, a $C_2$ to $C_{30}$ linear, saturated or unsaturated hydrocarbon radical, a phenyl radical, and/or an aryl radical. Non-limiting examples of the radicals represented by $R^1$ and $R^2$ include alkyl radicals such as methyl, ethyl, propyl, isopropyl, butyl, isobutyl, pentyl, isopentyl, neopentyl, amyl, isoamyl, hexyl, isohexyl and the like; alkenyl radicals such as vinyl, halovinyl, alkylvinyl, allyl, haloallyl, alkylallyl; cycloalkyl radicals such as cyclobutyl, cyclopentyl, cyclohexyl, and the like; phenyl radicals, benzyl radicals, halogenated hydrocarbon radicals such as 3-chloropropyl, 4-bromobutyl, 3,3,3-trifluoropropyl, chlorocyclohexyl, bromophenyl, chlorophenyl, and the like, and sulfur-containing radicals such as mercaptoethyl, mercaptopropyl, mercaptohexyl, mercaptophenyl, and the like; by preference, $R^1$ and $R^2$ are an alkyl radical that contains 1 to approximately 6 carbon atoms, and particularly preferably $R^1$ and $R^2$ are methyl. PE denotes a polyoxyalkylene radical. Preferred polyoxyalkylene radicals are derived from ethylene oxide, propylene oxide, and glycerol. The numbers x, y, and z are integers and range, mutually independently in each case, from 0 to 50,000. The molecular weights of the dimethicones are between 1000 D and 10,000,000 D. The viscosities are between 100 and 10,000,000 cPs, measured at 25° C. using a glass capillary viscosimeter in accordance with Dow Corning Corporate Test Method CTM 0004 of Jul. 20, 1970. Preferred viscosities are between 1000 and 5,000,000 cPs; very particularly preferred viscosities are between 10,000 und 3,000,000 cPs. The most preferred range is between 50,000 und 2,000,000 cPs.

Corresponding dimethicone copolyols are commercially obtainable and are marketed, for example, by the Dow Corning company under the designation Dow Corning® 5330 Fluid.

The teaching of the present invention also, of course, encompasses the fact that the dimethiconols, dimethicones, and/or dimethicone copolymers can already be present as an emulsion. The corresponding emulsion of the dimethiconols, dimethicones, and/or dimethicone copolyols can be manufactured both after manufacture of the corresponding dimethiconols, dimethicones, and/or dimethicone copolyols, from them and using usual emulsification methods known to the skilled artisan. For this purpose both cationic, anionic, nonionic, or zwitterionic surfactants and emulsifiers can be used, as auxiliaries, as adjuvants for manufacture of the corresponding emulsions. The emulsions of the dimethiconols, dimethicones, and/or dimethicone copolyols can of course also be manufactured directly by way of an emulsion polymerization method, Such methods, too, are very familiar to the skilled artisan.

If the dimethiconols, dimethicones, and/or dimethicone copolyols are used as an emulsion, the droplet size of the emulsified particles is then, according to the present invention, 0.01 to 10,000 μm, preferably 0.01 to 100 μm, particularly preferably 0.01 to 20 μm, and very particularly preferably 0.01 to 10 μm. The particle size is determined using the light-scattering method.

If branched dimethiconols, dimethicones, and/or dimethicone copolyols are used, this is to be understood to mean that the branching is greater than a random branching that occurs randomly as a result of contaminants in the respective monomers. "Branched" dimethiconols, dimethicones, and/or dimethicone copolyols are therefore to be understood, for purposes of the present invention, to mean that the degree of branching is greater than 0.01%. A degree of branching greater than 0.1% is preferred, and very particularly preferably it is greater than 0.5%. The degree of branching is determined from the ratio of unbranched monomers to the branching monomers, i.e. the quantity of tri- and tetrafunctional siloxanes. Both low-branching and high-branching dimethiconols, dimethicones, and/or dimethicone copolyols can be very particularly preferred according to the present invention.

Suitable silicones are, in addition, aminofunctional silicones (S4), in particular the silicones that are grouped under the INCI name Amodimethicone. These are to be understood as silicones that comprise at least one, optionally substituted, amino group.

Such silicones can be described, for example, by the formula

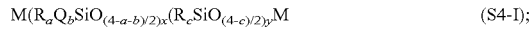

(S4-I);

in the above formula, R is a hydrocarbon or hydrocarbon radical having 1 to approximately 6 carbon atoms, Q is a polar radical of the general formula —$R^1Z$, in which $R^1$ is a bivalent bonding group that is bound to hydrogen and to the Z radical, assembled from carbon and hydrogen atoms, carbon, hydrogen, and oxygen atoms, or carbon, hydrogen, and nitrogen atoms, and Z is an organic aminofunctional radical that contains at least one aminofunctional group; "a" assumes values in the range from approximately 0 to approximately 2, "b" assumes values in the range from approximately 1 to approximately 3, "a"+"b" is less than or equal to 3, and "c" is a number in the range from approximately 1 to approximately 3, and x is a number in the range from 1 to approximately 2,000, preferably from approximately 3 to approximately 50, and most preferably from approximately 3 to approximately 25, and y is a number in the range from approximately 20 to approximately 10,000, preferably from approximately 125 to approximately 10,000, and most preferably from approximately 150 to approximately 1,000, and M is a suitable silicone terminal group that is known in the existing art, preferably trimethylsiloxy. Non-limiting examples of the radicals represented by R include alkyl radicals such as methyl, ethyl, propyl, isopropyl, isopropyl, butyl, isobutyl, amyl, isoamyl, hexyl, isohexyl and the like; alkenyl radicals such as vinyl, halovinyl, alkylvinyl, allyl, haloallyl, alkylallyl; cycloalkyl radicals such as cyclobutyl, cyclopentyl, cyclohexyl and the like; phenyl radicals, benzyl radicals, halocarbon radicals such as 3-chloropropyl, 4-bromobutyl, 3,3,3-trifluoropropyl, chlorocyclohexyl, bromophenyl, chlorophenyl, and the like, and sulfur-containing radicals such as mercaptoethyl, mercaptopropyl, mercaptohexyl, mercaptophenyl and the like; R is preferably an alkyl radical that contains 1 to approximately 6 carbon atoms, and R is most preferably methyl. Examples of $R^1$ include methylene, ethylene, propylene, hexamethylene, decamethylene, —$CH_2CH(CH_3)CH_2$—, phenylene, naphthylene, —$CH_2CH_2SCH_2CH_2$—, —$CH_2CH_2OCH_2$—, —$OCH_2CH_2$—, —$OCH_2CH_2CH_2$—, —$CH_2CH(CH_3)C(O)$$OCH_2$—, —$(CH_2)_3C(O)OCH_2CH_2$—, —$C_6H_4C_6H_4$—, —$C_6H_4CH_2C_6H_4$—, and —$(CH_2)_3C(O)SCH_2CH_2$—.

Z is an organic aminofunctional radical containing at least one functional amino group. One possible formula for Z is $NH(CH_2)_zNH_2$, in which z denotes an integer from 1 to 50. Another possible formula for Z is —$NH(CH_2)_zNH(CH_2)_{zz}$, in which both z and zz denote, mutually independently, an integer from 1 to 50; this structure encompasses diamino ring structures such as piperazinyl. Z is particularly preferably a —$NHCH_2CH_2NH_2$ radical. Another possible formula for Z is —$N(CH_2)_zNX^1X^2$ or —$NX^1X^2$, in which $X^1$ and $X^2$ are selected, mutually independently in each case, from hydrogen and a hydrocarbon radical having from 1 to approximately 6 carbon atoms.

Very particularly preferably, Q denotes a polar aminofunctional radical of the formula —$CH_2CH_2CH_2NHCH_2CH_2NH_2$.

The molar ratio of the $R_aQ_bSiO_{(4-a-b)/2}$ units to the $R^cSiO_{(4-c)/2}$ units is in the range from approximately 1:2 to 1:65, by preference from approximately 1:5 to approximately 1:65, and particularly preferably from approximately 1:15 to approximately 1:20. If one or more silicones of the above formula are used, the different variable substituents in the above formula can the be different in the different silicone components that are present in the silicone mixture.

Preferred aminofunctional silicones correspond to the formula (S4-II)

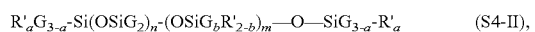
(S4-II), in which
G is —H, a phenyl group, —OH, —O—$CH_3$, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, —$C(CH_3)_3$;

a denotes a number between 0 and 3, in particular 0;
b denotes a number between 0 and 1, in particular 1,
m and n are numbers whose sum (m+n) is between 1 and 2000, preferably between 50 and 150, n preferably assuming values from 0 to 1999 and in particular from 49 to 149, and m preferably assuming values from 1 to 2000, in particular from 1 to 10;
R' is a monovalent radical selected from
—N(R")—$CH_2$—$CH_2$—N(R")$_2$
—N(R")$_2$
—$N^+(R")_3A^-$
—$N^+H(R")_2A^-$
—$N^+H_2(R")A^-$
—N(R")—$CH_2$—$CH_2$—$N^+R''H_2A^-$, each R" denoting identical or different radicals from the group of —H, phenyl, benzyl, the $C_{1-20}$ alkyl radicals, preferably —$CH_3$, —$CH_2CH_3$, —$CH_2CH_2CH_3$, —$CH(CH_3)_2$, —$CH_2CH_2CH_2H_3$, —$CH_2CH(CH_3)_2$, —$CH(CH_3)CH_2CH_3$, —$C(CH_3)_3$, and A representing an anion that is preferably selected from chloride, bromide, iodide, or methosulfate.

Particularly preferred aminofunctional silicones correspond to formula (S4-III)

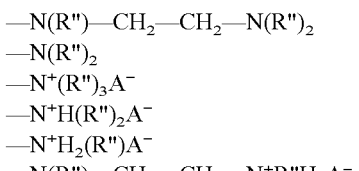

in which m and n are numbers whose sum (m+n) is between 1 and 2000, preferably between 50 and 150, n preferably assuming values from 0 to 1999 and in particular from 49 to 149, and m preferably assuming values from 1 to 2000, in particular from 1 to 10.

These silicones are referred to according to the INCI declaration as Trimethylsilylamodimethicones.

Also particularly preferred are aminofunctional silicones of formula (S4-IV)

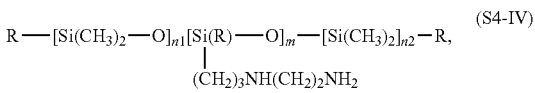

in which R denotes —OH, —O—$CH_3$, or a —$CH_3$ group, and m, n1, and n2 are numbers whose sum (m+n1+n2) is between 1 and 2000, preferably between 50 and 150, the sum (n1+n2) preferably assuming values from 0 to 1999 and in particular from 49 to 149, and m preferably assuming values from 1 to 2000, in particular from 1 to 10.

These silicones are referred to according to the INCI declaration as Amodimethicones, and are available, for example, in the form of an emulsion as the commercial product Dow Corning® 949, mixed with a cationic and a nonionic surfactant.

The aminofunctional silicones used are by preference those that have an amine number above 0.25 meq/g, preferably above 0.3 meq/g, and particularly preferably above 0.4 meq/g. The amine number denotes the milliequivalent of amine per gram of the aminofunctional silicone. It can be ascertained by titration, and is also indicated with the "mg KOH/g" unit.

Further suitable silicones are, for example,
- oligomeric polydimethylcyclosiloxanes (INCI name: Cyclomethicone), in particular the tetrameric and the pentameric compound, which are marketed by Dow Corning as commercial products DC 344, DC 245 Fluid, and DC 345, respectively;
- hexamethyldisiloxane (INCI name: Hexamethyldisiloxane), e.g. the product marketed under the designation Abil® K 520;
- polyphenylmethylsiloxanes (INCI name: Phenyl Trimethicone), e.g. the commercial product DC 556 Cosmetic Grade Fluid of Dow Corning;
- esters and partial esters of the silicone-glycol copolymers such as those marketed, for example, by the Fanning company under the commercial designation Fancorsil® LIM (INCI name: Dimethicone Copolyol Meadowfoamate);
- anionic silicone oils such as, for example, the product Dow Corning® 1784.

According to a preferred embodiment, the agent according to the present invention contains at least two different silicone derivatives, particularly preferably a combination of a volatile and a non-volatile silicone. Those silicones that exhibit a volatility equal to or greater than the volatility of cyclic pentameric dimethylsiloxane are "volatile" for purposes of the invention. Such combinations are also available as commercial products (e.g. Dow Corning® 1401, Dow Corning® 1403, and Dow Corning® 1501, in each case mixtures of a cyclomethicone and a dimethiconol).

Preferred mixtures of different silicones are, for example, dimethicones and dimethiconols, linear dimethicones, and cyclic dimethiconols. A very particularly preferred mixture of silicones is constituted from at least one cycle dimethiconol and/or dimethicone, at least one further non-cyclic dimethicone and/or dimethiconol, and at least one aminofunctional silicone.

If different silicones are used as a mixture, the mixing ratio is largely variable. Preferably, however, all the silicones used for mixing are utilized at a ratio from 5:1 to 1:5 in the case of a binary mixture. A ratio from 1:3 to 3:1 is particularly preferred. Very particularly preferred mixtures contain all the silicones contained in the mixture very largely at a ratio of approximately 1:1, based in each case on the quantity used in wt %.

The agents contain the silicones preferably in quantities from 1 to 25 wt %, particularly preferably from 5 to 20 wt %, and particularly preferably from 7 to 15 wt %, based in each case on the entire agent.

Although the agent according to the present invention by preference contains a silicone derivative as a care-providing agent, it is also possible for the agent to contain, instead of or in addition to a silicone component, at least one care-providing substance of a different class of compound.

The agent can, for example, contain at least one protein hydrolysate and/or one of its derivatives as a care-providing substance of a different class of compound.

Protein hydrolysates are product mixtures obtained by the acid-, base-, or enzyme-catalyzed breakdown of proteins. The term "protein hydrolysates" is also understood according to the present invention as total hydrolysates as well as individual amino acids and their derivatives, as well as mixtures of different amino acids. Polymers constructed from amino acids and amino-acid derivatives are also understood according to the present invention under the term "protein hydrolysates". Included among the latter are, for example, polyalanine, polyasparagine, polyserine, etc. Further examples of compounds usable according to the present invention are L-alanyl-L-proline, polyglycine, glycyl-L-glutamine, or D/L-methionine-5-methylsulfonium chloride. β-Amino acids and their derivatives, such as β-alanine, anthranilic acid, or hippuric acid, can of course also be used according to the present invention. The molecular weight of the protein hydrolysates usable according to the present invention is between 75 (the molecular weight of glycine) and 200,000; the molecular weight is preferably 75 to 50,000 dalton, and very particularly preferably 75 to 20,000 dalton.

According to the present invention, protein hydrolysates of both plant and animal origin, or of marine or synthetic origin, can be used.

Animal protein hydrolysates are, for example, hydrolysates of elastin, collagen, keratin, silk, and milk protein, which can also be present in the form of salts. Such products are marketed, for example, under the trademarks Dehylan® (Cognis), Promois® (Interorgana), Collapuron® (Cognis), Nutrilan® (Cognis), Geiita-Sol® (Deutsche Gelatine Fabriken Stoess & Co), Lexein® (Inolex), Sericin (Pentapharm), and Kerasol® (Croda).

The use of silk protein hydrolysates is of particular interest, "Silk" is understood as the fibers of the cocoon of the mulberry silkworm (*Bombyx mori* L.). The raw silk fiber is made up of a double thread of fibroin. Sericin serves as a glue substance holding this double thread together. Silk is made up of 70 to 80 wt % fibroin, 19 to 28 wt % sericin, 0.5 to 1 wt % fat, and 0.5 to 1 wt % coloring agents and mineral constituents.

The essential constituents of sericin are approximately 46 wt % hydroxyamino acids. Sericin is made up of a group of 5 to 6 proteins. The essential amino acids of sericin are serine (Ser, 37 wt %), aspartate (Asp, 26 wt %), glycine (Gly, 17 wt %), alanine (Ala), leucine (Leu), and tyrosine (Tyr).

Water-insoluble fibroin is included among the scleroproteins having a long-chain molecular structure. The principal constituents of fibroin are glycine (44 wt %), alanine (26 wt %), and tyrosine (13 wt %). A further essential structural feature of fibroin is the hexapeptide sequence Ser-Gly-Ala-Gly-Ala-Gly.

It is technically simple to separate the two silk proteins from one another. It is therefore not surprising that both sericin and fibroin are known, each individually, as raw materials for use in cosmetic products. Protein hydrolysates and derivatives based on the respective individual silk proteins are also known raw materials in cosmetic agents. For example, sericin as such is marketed by Pentapharm Ltd. as a commercial product with the designation Sericin Code 303-02. Fibroin is offered far more frequently on the market as a protein hydrolysate, at various molecular weights. These hydrolysates are marketed in particular as "silk hydrolysates." Hydrolyzed fibroin having average molecular weights between 350 and 1000 is marketed, for example, under the commercial designation Promois® Silk.

The positive properties of the silk protein derivatives from sericin and fibroin, individually for each one, are known in the literature. For example, the sales brochure of the Pentapharm company describes the cosmetic effects of sericin on the skin as irritation-soothing, hydrating, and film-forming. The effect of a fibroin derivative is described, for example in DE 31 39 438 A1, as providing care to and revival of the hair. According to DE 102 40 757 A1, with the simultaneous use of sericin and fibroin, or derivatives and/hydrolysates thereof, it is furthermore possible to achieve a synergistic increase in the positive effects of the silk proteins and their derivatives.

It is therefore preferred to use in the agent according to the present invention, as a silk protein hydrolysate, an active-substance complex (A) comprising the active substance (A1)

selected from sericin, sericin hydrolysates, and/or derivatives thereof, as well as mixtures thereof, and an active substance (A2) selected from fibroin and/or fibroin hydrolysates and/or derivatives thereof and/or mixtures thereof.

The active-substance complex (A) significantly improves, in synergistic fashion, the essential internal and external structural features presented above, and both the strength and elasticity of human hairs.

The following can be used as active substances (A1) in the active-substance complex (A):

natural sericin;

hydrolyzed and/or further derivatized sericin, for example commercial products having the INCI names Sericin, Hydrolyzed Sericin, or Hydrolyzed Silk;

a mixture of the amino acids serine, aspartate, and glycine and/or the methyl, propyl, isopropyl, butyl, isobutyl esters thereof, the salts thereof such as, for example, hydrochlorides, sulfates, acetates, citrates, tartrates, such that the serine and/or derivatives thereof are contained in said mixture at 20 to 60 wt %, the aspartate and/or derivatives thereof at 10 to 40 wt %, and the glycine and/or derivatives thereof at 5 to 30 wt %, with the stipulation that the quantities of said amino acids and/or derivatives thereof by preference add up to 100 wt %; and mixtures thereof.

The following can be used as active substances (A2) in the active-substance complex (A):

natural fibroin converted into a soluble form;

hydrolyzed and/or further derivatized fibroin, especially partly hydrolyzed fibroin, which contains as a principal constituent the amino acid sequence Ser-Gly-Ala-Gly-Ala-Gly;

the amino acid sequence Ser-Gly-Ala-Gly-Ala-Gly;

a mixture of the amino acids glycine, alanine, and tyrosine and/or the methyl, propyl, isopropyl, butyl, isobutyl esters thereof, the salts thereof such as, for example, hydrochlorides, sulfates, acetates, citrates, tartrates, such that the glycine and/or derivatives thereof is contained in said mixture in quantities from 20 to 60 wt %, the alanine and derivatives thereof in quantities from 10 to 40 wt %, and the tyrosine and derivatives thereof in quantities from 0 to 25 wt %, with the stipulation that the quantities of said amino acids and/or derivatives thereof by preference add up to 100 wt %; and mixtures thereof.

Particularly good care-providing properties can be achieved if one of the two active-substance components of the active-substance complex (A) is used in the natural or, if need be, solubilized form. It is also possible to utilize a mixture of several active substances (A1) and/or (A2).

It can be preferred for the two active substances (A1) and (A2) to be used in the agents according to the present invention at a ratio from 10:90 to 70:30, in particular 15:85 to 50:50, and very particularly 20:80 to 40:60, based on their respective active-substance contents.

The derivatives of the hydrolysates of sericin and fibroin encompass both anionic and cationized protein hydrolysates. The protein hydrolysates of sericin and fibroin, and the derivatives manufactured therefrom, can be obtained from the corresponding proteins by way of a chemical, in particular alkaline or acid, hydrolysis, by an enzymatic hydrolysis, and/or by a combination of the two types of hydrolysis. The hydrolysis of proteins generally yields a protein hydrolysate having a molecular weight distribution from approximately 100 daltons to several thousand daltons. Those protein hydrolysates of sericin and fibroin and/or derivatives thereof whose underlying protein fraction has a molecular weight from 100 to 25,000 daltons, preferably 250 to 10,000 daltons, are preferred. Quaternized amino acids and mixtures thereof are also to be understood as cationic protein hydrolysates of sericin and fibroin. Quaternization of the protein hydrolysates or amino acids is often carried out by means of quaternary ammonium salts such as, for example, N,N-dimethyl-N-(n-alkyl)-N-(2-hydroxy-3-chloro-n-propyl)ammonium halides. The cationic protein hydrolysates can moreover be even further derivatized. Typical examples that may be mentioned of cationic protein hydrolysates and derivatives usable according to the present invention are the following products listed under the INCI names in the "International Cosmetic Ingredient Dictionary and Handbook," (seventh edition 1997, The Cosmetic, Toiletry, and Fragrance Association, 1101 17$^{th}$ Street, N.W., Suite 300, Washington, D.C. 20036-4702), and available commercially: Cocodimonium Hydroxypropyl Hydrolyzed Silk, Cocodimonium Hydroxypropyl Silk Amino Acids, Hydroxypropyltrimonium Hydrolyzed Silk, Lauryldimonium Hydroxypropyl Hydrolyzed Silk, Steardimonium Hydroxypropyl Hydrolyzed Silk, Quaternium-79 Hydrolyzed Silk. Typical examples that may be mentioned of the anionic protein hydrolysates and derivatives according to the present invention are the following products listed under the INCI names in the "International Cosmetic Ingredient Dictionary and Handbook," (seventh edition 1997, The Cosmetic, Toiletry, and Fragrance Association, 1101 17th Street, N.W., Suite 300, Washington, D.C. 20036-4702), and commercially available: Potassium Cocoyl Hydrolyzed Silk, Sodium Lauroyl Hydrolyzed Silk, or Sodium Stearoyl Hydrolyzed Silk. Lastly, the following products obtainable commercially under their INCI names may be mentioned as typical examples of the derivatives of sericin and fibroin usable according to the present invention: Ethyl Ester of Hydrolyzed Silk, and Hydrolyzed Silk PG-Propyl Methylsilanediol. Also usable according to the present invention, although not unconditionally preferred, are the commercially obtainable products having the INCI names Palmitoyl Oligopeptide, Palmitoyl Pentapeptide-3, Palmitoyl Pentapeptide-2, Acetyl Hexapeptide-1, Acetyl Hexapeptide-3, Copper Tripeptide-1, Hexapeptide-1, Hexapeptide-2, and MEA-Hydrolyzed Silk.

The effect of the active substance complex (A) can be further enhanced by fatty substances. "Fatty substances" are to be understood as fatty acids, fatty alcohols, natural and synthetic waxes that can be present both in solid form and in liquid form in aqueous dispersion, and natural and synthetic cosmetic oil components.

Protein hydrolysates of vegetable origin, e.g. soy, almond, bean, potato, and wheat protein hydrolysates, are obtainable, for example, under the trademarks Gluadin® (Cognis), DiaMin® (Diamalt), Lexein® (Inolex), Hydrosoy® (Croda), Hydrolupin® (Croda), Hydrosesame® (Croda), Hydrotritium® (Croda), and Crotein® (Croda).

Although the use of protein hydrolysates per se is preferred, it is also optionally possible to use instead of them, if applicable, amino-acid mixtures obtained in different fashion. It is likewise possible to use derivatives of protein hydrolysates, for example in the form of their fatty acid condensation products. Such products are marketed, for example, under the designations Lamepon® (Cognis), Lexein® (Inolex), Crolastin® (Croda), Crosilk® (Croda), or Crotein® (Croda).

The teaching according to the present invention of course encompasses all isomeric forms, such as cis-trans isomers, diastereomers, and chiral isomers.

It is also possible according to the present invention to utilize a mixture of several protein hydrolysates.

The protein hydrolysates are contained in the agents according to the present invention, for example, in concentrations from 0.01 wt % to 20 wt %, by preference from 0.05 wt % to 15 wt %, and very particularly preferably in quantities from 0.05 wt % to 5 wt %, based in each case on the entire application preparation.

Cationic surfactants are also suitable as a care-providing substance of a different class of compound.

The cationic surfactants of the quaternary ammonium compound, esterquat, and amidoamine types are preferred according to the present invention, Preferred quaternary ammonium compounds are ammonium halides, in particular chlorides and bromides, such as alkyltrimethylammonium chlorides, dialkyldimethylammonium chlorides, and trialkylmethylammonium chlorides, e.g. cetyltrimethylammonium chloride, stearyltrimethylammonium chloride, distearyidimethylammonium chloride, lauryldimethylammonium chloride, lauryldimethylbenzylammonium chloride, and tricetylmethylammonium chloride, as well as the imidazolium compounds known by the INCI names Quaternium-27 and Quaternium-83. The long alkyl chains of the aforementioned surfactants preferably have 10 to 18 carbon atoms.

Esterquats are known substances that contain both at least one ester function and at least one quaternary ammonium group as a structural element. Preferred esterquats are quaternized ester salts of fatty acids with triethanolamine, quaternized ester salts of fatty acids with diethanolalkylamines, and quaternized ester salts of fatty acids with 1,2-dihydroxypropyldialkylamines. Such products are marketed, for example, under the trademarks Stepantex®, Dehyquart®, and Armocare®. Examples of such esterquats are the products Armocare® VGH-70—an N,N-bis(2-palmitoyloxyethyl)dimethylammonium chloride—as well as Dehyquart® F-75, Dehyquart® C-4046, Dehyquart® L-80, and Dehyquart® AU-35.

The alkylamidoamines are usually produced by amidation of natural or synthetic fatty acids and fatty acid cuts with dialkylaminoamines. One compound from this group of substances that is particularly suitable according to the present invention is the stearamidopropyldimethylamine available commercially under the designation Tegoamid® S18.

The cationic surfactants are contained in the agents according to the present invention preferably in quantities from 0.05 to 10 wt %, based on the entire application preparation. Quantities from 0.1 to 5 wt % are particularly preferred.

Care-providing polymers are also suitable as a care-providing substance. Be it noted at this juncture that some care-providing polymers also exhibit film-forming and/or setting properties, and can therefore also be recited when listing suitable film-forming and/or setting polymers.

A first group of care-providing polymers is the cationic polymers. "Cationic polymers" are to be understood as polymers that comprise in the main chain and/or side chain a group that can be "temporarily" or "permanently" cationic. According to the present invention, those polymers that possess a cationic group regardless of the pH of the agent are referred to as "permanently cationic." These are, as a rule, polymers that contain a quaternary nitrogen atom, for example in the form of an ammonium group. Preferred cationic groups are quaternary ammonium groups. In particular, those polymers in which the quaternary ammonium group is bound via a $C_{1-4}$ hydrocarbon group to a main polymer chain made up of acrylic acid, methacrylic acid, or derivatives thereof, have proven to be particularly suitable.

Homopolymers of the general formula (G1-I),

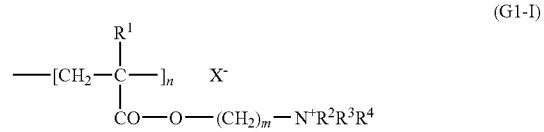

in which $R^1$=—H or —$CH_3$, $R^2$, $R^3$ and $R^4$ are selected, mutually independently, from $C_{1-4}$ alkyl, alkenyl, or hydroxyalkyl groups, m=1, 2, 3 or 4, n is a natural number, and $X^-$ is a physiologically acceptable organic or inorganic anion, as well as copolymers made up substantially of the monomer units presented in formula (G1-I) as well as nonionogenic monomer units, are particularly preferred cationic polymers. In the context of these polymers, those for which at least one of the following conditions apply are preferred according to the present invention:

$R^1$ denotes a methyl group
$R^2$, $R^3$ and $R^4$ denote methyl groups
m has the value of 2.

Possibilities as physiologically acceptable counterions $X^-$ are, for example, halide ions, sulfate ions, phosphate ions, methosulfate ions, and organic ions such as lactate, citrate, tartrate, and acetate ions. Halide ions, in particular chloride, are preferred.

A particularly suitable homopolymer is the poly(methacryloyloxyethyltrimethylammonium chloride) (crosslinked, if desired) having the INCI name Polyquaternium-37. The crosslinking can be accomplished, if desired, with the aid of polyolefinically unsaturated compounds, for example divinylbenzene, tetraallyloxyethane, methylene bisacrylamide, diallyl ether, polyallylpolyglyceryl ether, or allyl ethers of sugars or sugar derivatives such as erythritol, pentaerythritol, arabitol, mannitol, sorbitol, sucrose, or glucose. Methylene bisacrylamide is a preferred cross-linking agent.

The homopolymer is preferably used in the form of a nonaqueous polymer dispersion that should comprise a polymer proportion not less than 30 wt %. Such polymer dispersions are obtainable commercially under the designations Salcare® SC 95 (approx. 50% polymer proportion, further components: mineral oil (INCI name: Mineral Oil) and tridecylpolyoxypropylenepolyoxyethylene ether (INCI name: PPG-1-Trideceth-6)), and Salcare® SC 96 (approx. 50% polymer proportion, further components: mixture of diesters of propylene glycol with a mixture of caprylic and capric acid (INCI name: Propylene Glycol Dicaprylate/Dicaprate) and tridecylpolyoxypropylenepolyoxyethylene ether (INCI name: PPG-1-Trideceth-6)).

Copolymers having monomer units according to formula (G1-I) preferably contain acrylamide, methacrylamide, acrylic acid $C_{1-4}$ alkyl esters, and methacrylic acid $C_{1-4}$ alkyl esters as nonionogenic monomer units. Of these nonionogenic monomers, acrylamide is particularly preferred. These copolymers as well, as in the case of the homopolymers described above, can be crosslinked. A copolymer preferred according to the present invention is the crosslinked copolymer of acrylamide and methacryloyloxyethyltrimethylammonium chloride. Such copolymers, in which the monomers are present at a weight ratio of approximately 20:80, are commercially obtainable, as an approx. 50% nonaqueous polymer dispersion, under the designation Salcare® SC 92.

Additional preferred cationic polymers are, for example;

quaternized cellulose derivatives such as those obtainable commercially under the designations Celquat® and Polymer JR®. The compounds Celquat® H 100, Celquat® L 200, and Polymer JR® 400 are preferred quaternized cellulose derivatives;

cationic alkyl polyglycosides according to DE Patent 44 13 686;

cationized honey, for example the commercial product Honeyquat® 50;

cationic guar derivatives such as, in particular, the products marketed under the trade names Cosmedia® Guar and Jaguar®;

polysiloxanes having quaternary groups, such as, for example, the commercially obtainable products Q2-7224 (manufacturer: Dow Corning; a stabilized trimethylsilylamodimethicone), Dow Corning® 929 Emulsion (containing a hydroxylamino-modified silicone that is also referred to as Amodimethicone), SM-2059 (manufacturer: General Electric), SLM-55067 (manufacturer: Wacker), and Abil®-Quat 3270 and 3272 (manufacturer: Th. Goldschmidt; diquaternary polydimethylsiloxanes, Quaternium-80);

polymeric dimethyldiallylammonium salts and copolymers thereof with esters and amides of acrylic acid and methacrylic acid. The products available commercially under the designations Merquat® 100 (poly(dimethyldiallylammonium chloride)) and Merquat® 550 (dimethyldiallylammonium chloride/acrylamide copolymer) are examples of such cationic polymers;

copolymers of vinylpyrrolidone with quaternized derivatives of dialkylaminoalkyl acrylate and methacrylate, such as, for example, vinylpyrrolidone/dimethylaminoethylmethacrylate copolymers quaternized with diethyl sulfate. Such compounds are obtainable commercially under the designations Gafquat® 734 and Gafquat® 755;

vinylpyrrolidone/vinylimidazolium methochloride copolymers, such as those offered under the designations Luviquat® FC 370, FC 550, FC 905, and HM 552;

quaternized poly(vinylalcohol); and the polymers known under the designations Polyquaternium-2, Polyquaternium-17, Polyquaternium-18, and Polyquaternium-27, having quaternary nitrogen atoms in the main polymer chain.

The polymers known under the designations Polyquaternium-24 (commercial product e.g. Quatrisoft® LM 200) can similarly be used as cationic polymers. Likewise usable according to the present invention are the copolymers of vinylpyrrolidone such as those available as the commercial products Copolymer 845 (manufacturer: ISP), Gaffix® VC 713 (manufacturer: ISP), Gafquat® ASCP 1011, Gafquat® HS110, Luviquat®8155, and Luviquat® MS 370.

Additional cationic polymers usable according to the present invention are the so-called "temporarily cationic" polymers. These polymers usually contain an amino group that is present at certain pH values as a quaternary ammonium group and therefore cationically. Chitosan and its derivatives, such as those readily available commercially, for example, under the commercial designations Hydagen® CMF, Hydagen® HCMF, Kytamer® PC, and Chitolam® NB/101, are, for example, preferred.

Cationic polymers that are preferred for use according to the present invention are cationic cellulose derivatives and chitosan and its derivatives, in particular the commercial products Polymer® JR 400, Hydagen® HCMF, and Kytamer® PC, cationic guar derivatives, cationic honey derivatives, in particular the commercial product Honeyquat® 50, cationic alkyl polyglycosides according to DE Patent 44 13 686, and polymers of the Polyquaternium-37 type.

Also to be listed among the cationic polymers are cationized protein hydrolysates, in which context the underlying protein hydrolysate can derive from animals, for example from collagen, milk, or keratin, from plants, for example from wheat, corn, rice, potatoes, soy, or almonds, from marine life forms, for example from fish collagen or algae, or from biotechnologically obtained protein hydrolysates. The protein hydrolysates serving as the basis for the cationic derivatives according to the present invention can be obtained from the corresponding proteins by way of a chemical, in particular alkaline or acid, hydrolysis, by an enzymatic hydrolysis, and/or by a combination of both types of hydrolysis. The hydrolysis of proteins results, as a rule, in a protein hydrolysate having a molecular weight distribution from approximately 100 dalton up to several thousand dalton. Those cationic protein hydrolysates whose underlying protein component has a molecular weight from 100 to 25,000 dalton, preferably 250 to 5,000 dalton, are preferred. Also to be understood as cationic protein hydrolysates are quaternized amino acids and mixtures thereof. Quaternization of the protein hydrolysates or amino acids is often carried out by means of quaternary ammonium salts such as, for example, N,N-dimethyl-N-(n-alkyl)-N-(2-hydroxy-3-chloro-n-propyl)ammonium halides. The cationic protein hydrolysates can furthermore also be further derivatized. Typical examples that may be mentioned of cationic protein hydrolysates and derivatives are the following products listed under the INCI names in the "International Cosmetic Ingredient Dictionary and Handbook," (seventh edition 1997, The Cosmetic, Toiletry, and Fragrance Association, 1101 17$^{th}$ Street, N.W., Suite 300, Washington, D.C. 20036-4702), and available commercially: Cocodimonium Hydroxypropyl Hydrolyzed Collagen, Cocodimonium Hydroxypropyl Hydrolyzed Casein, Cocodimonium Hydroxypropyl Hydrolyzed Collagen, Cocodimonium Hydroxypropyl Hydrolyzed Hair Keratin, Cocodimonium Hydroxypropyl Hydrolyzed Keratin, Cocodimonium Hydroxypropyl Hydrolyzed Rice Protein, Cocodimonium Hydroxypropyl Hydrolyzed Soy Protein, Cocodimonium Hydroxypropyl Hydrolyzed Wheat Protein, Hydroxypropyl Arginine Lauryl/Myristyl Ether HCl, Hydroxypropyltrimonium Gelatin, Hydroxypropyltrimonium Hydrolyzed Casein, Hydroxypropyltrimonium Hydrolyzed Collagen, Hydroxypropyltrimonium Hydrolyzed Conchiolin Protein, Hydroxypropyltrimonium Hydrolyzed Keratin, Hydroxypropyltrimonium Hydrolyzed Rice Bran Protein, Hydroxypropyltrimonium Hydrolyzed Soy Protein, Hydroxypropyl Hydrolyzed Vegetable Protein, Hydroxypropyltrimonium Hydrolyzed Wheat Protein, Hydroxypropyltrimonium Hydrolyzed Wheat Protein/Siloxysilicate, Laurdimonium Hydroxypropyl Hydrolyzed Soy Protein, Laurdimonium Hydroxypropyl Hydrolyzed Wheat Protein, Laurdimonium Hydroxypropyl Hydrolyzed Wheat Protein/Siloxysilicate, Lauryldimonium Hydroxypropyl Hydrolyzed Casein, Lauryldimonium Hydroxypropyl Hydrolyzed Collagen, Lauryldimonium Hydroxypropyl Hydrolyzed Keratin, Lauryldimonium Hydroxypropyl Hydrolyzed Soy Protein, Steardimonium Hydroxypropyl Hydrolyzed Casein, Steardimonium Hydroxypropyl Hydrolyzed Collagen, Steardimonium Hydroxypropyl Hydrolyzed Keratin, Steardimonium Hydroxypropyl Hydrolyzed Rice Protein, Steardimonium Hydroxypropyl Hydrolyzed Soy Protein, Steardimonium Hydroxypropyl Hydrolyzed Vegetable Protein, Steardimonium Hydroxypropyl Hydrolyzed Wheat Protein, Steartrimonium Hydroxyethyl Hydrolyzed Collagen, Quaternium-76

Hydrolyzed Collagen, Quaternium-79 Hydrolyzed Collagen, Quaternium-79 Hydrolyzed Keratin, Quaternium-79 Hydrolyzed Milk Protein, Quaternium-79 Hydrolyzed Soy Protein, Quaternium-79 Hydrolyzed Wheat Protein.

The plant-based cationic protein hydrolysates and derivatives are very particularly preferred.

Amphoteric polymers used in preferred fashion are those polymerizates made up substantially of
(b) monomers having quaternary ammonium groups of the general formula (II)

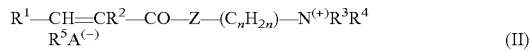

(II)

in which $R^1$ and $R^2$, mutually independently, denote hydrogen or a methyl group, and $R^3$, $R^4$ and $R^5$, each mutually independently, denote an alkyl group having 1 to 4 carbon atoms, Z denotes an NH group or an oxygen atom, n is an integer from 2 to 5, and $A^{(-)}$ is the anion of an organic or inorganic acid; and
(c) monomeric carboxylic acids of the general formula (III)

(III)

in which $R^6$ and $R^7$, mutually independently, denote hydrogen or a methyl group.

These compounds can be used according to the present invention both directly and in the form of salts that are obtained by neutralization of the polymerizates, for example using an alkaline hydroxide. Those polymerizates in which monomers from among type (a) are used in which $R^3$, $R^4$, and $R^5$ are methyl groups, Z is an NH group, and $A^{(-)}$ is a halide, methoxysulfate, or ethoxysulfate ion, are very particularly preferred; acrylamidopropyltrimethylammonium chloride is a particularly preferred monomer (a). Acrylic acid is preferably used as monomer (b) for the aforesaid polymerizates.

The agents according to the present invention contain the care-providing cationic and/or amphoteric polymers preferably in a quantity from 0.01 to 5 wt %, in particular in a quantity from 0.1 to 2 wt %, based in each case on the entire application preparation.

The agent according to the present invention can further contain at least one vitamin, provitamin, vitamin precursor, and/or one of their derivatives as a care-providing substance.

Those vitamins, provitamins, and vitamin precursors that are usually assigned to groups A, B, C, E, F, and H are preferred according to the present invention.

The group of substances referred to as vitamin A includes retinol (vitamin $A_1$) as well as 3,4-didehydroretinol (vitamin $A_2$). β-Carotene is the provitamin of retinol. Vitamin A components that are suitable according to the present invention are, for example, vitamin A acid and its esters, vitamin A aldehyde, and vitamin A alcohol, as well as its esters such as the palmitate and acetate. The agents contain the vitamin A component preferably in quantities from 0.05 to 1 wt % based on the entire application preparation.

Members of the vitamin B group or vitamin B complex are, among others:
Vitamin $B_1$ (thiamine)
Vitamin $B_2$ (riboflavin)
Vitamin $B_3$. The compounds nicotinic acid and nicotinic acid amide (niacinamide) are often listed under this designation. Nicotinic acid amide is preferred according to the present invention; it is contained in the agents according to the present invention preferably in quantities from 0.05 to 1 wt % based on the entire application preparation.
Vitamin $B_5$ (pantothenic acid, panthenol, and pantolactone). Panthenol and/or pantolactone are preferably used in the context of this group. Derivatives of panthenol usable according to the present invention are, in particular, the esters and ethers of panthenol as well as cationically derivatized panthenols. Individual representatives are, for example, panthenol triacetate, panthenol monoethyl ether and its monoacetate, and cationic panthenol derivatives. The aforesaid compounds of the vitamin $B_5$ type are contained in the agents according to the present invention preferably in quantities from 0.05 to 10 wt % based on the entire application preparation. Quantities from 0.1 to 5 wt % are particularly preferred.
Vitamin $B_6$ (pyridoxine as well as pyridoxamine and pyridoxal). The aforesaid compounds of the vitamin $B_6$ type are contained in the agents according to the present invention preferably in quantities from 0.01 to 5 wt % based on the entire application preparation. Quantities from 0.05 to 1 wt % are particularly preferred.
Vitamin C (ascorbic acid). Vitamin C is utilized in the agents according to the present invention preferably in quantities from 0.1 to 3 wt % based on the entire application preparation. Utilization in the form of the palmitic acid ester, the glucosides or the phosphates can be preferred. Utilization in combination with tocopherols can likewise be preferred.
Vitamin E (tocopherols, in particular α-tocopherol). Tocopherol and its derivatives, which include in particular the esters such as the acetate, nicotinate, phosphate, and succinate, are contained in the agents according to the present invention preferably in quantities from 0.05 to 1 wt % based on the entire application preparation.
Vitamin F. The term "vitamin F" is usually understood as essential fatty acids, in particular linoleic acid, linolenic acid, and arachidonic acid.
Vitamin H. This refers to (3aS,4S,6aR)-2-oxohexahydrothienol[3,4-d]-imidazole-4-valeric acid, for which the trivial name "biotin" has nevertheless since become established. Biotin is contained in the agents according to the present invention preferably in quantities from 0.0001 to 1.0 wt %, in particular in quantities from 0.001 to 0.01 wt %, based in each case on the entire application preparation.

The agents according to the present invention preferably contain vitamins, provitamins, and vitamin precursors from groups A, B, C, E and H.

Panthenol, pantolactone, pyridoxine and its derivatives, as well as nicotinic acid amide and biotin, are particularly preferred.

D-panthenol is used very particularly preferably as a care-providing substance, if applicable in combination with at least one of the aforesaid silicone derivatives.

The agents according to the present invention can further contain at least one plant extract as a care-providing substance.

These extracts are usually produced by extraction of the entire plant. In individual cases, however, it may also be preferred to produce the extracts exclusively from blossoms and/or leaves of the plant.

With regard to the plant extracts usable according to the present invention, reference is made in particular to the extracts that are listed in the table beginning on page 44 of the 3rd edition of the Guideline for declaring the contents of cosmetic agents [Leitfaden zur Inhaltsstoffdeklaration kosmetischer Mittel], published by the Association of the personal hygiene and washing agents industry [Industrieverband Körperpflege-und Waschmittel e.V. (IKW)], Frankfurt.

According to the present invention the extracts from green tea, oak bark, nettle, hamamelis, hops, henna, chamomile, burdock root, horsetail, hawthorn, linden blossoms, almond, aloe vera, pine needles, horse chestnut, sandalwood, juniper, coconut, mango, apricot, lemon, wheat, kiwi fruit, melon, orange, grapefruit, salvia, rosemary, birch, mallow, lady's-smock, wild thyme, yarrow, thyme, lemon balm, restharrow, coltsfoot, hibiscus, meristem, ginseng, and ginger root are especially preferred.

Particularly preferred are the extracts from green tea, oak bark, nettle, hamamelis, hops, chamomile, burdock root, horsetail, linden blossoms, almond, aloe vera, coconut, mango, apricot, lemon, wheat, kiwi fruit, melon, orange, grapefruit, salvia, rosemary, birch, lady's-smock, wild thyme, yarrow, restharrow, meristem, ginseng, and ginger root.

The extracts from green tea, almond, aloe vera, coconut, mango, apricot, lemon, wheat, kiwi fruit, and melon are very particularly suitable.

Water, alcohols, and mixtures thereof can be used as extraction agents for manufacturing the aforesaid plant extracts. Among the alcohols, lower alcohols such as ethanol and isopropanol, but in particular polyvalent alcohols such as ethylene glycol and propylene glycol, both as the only extraction agent and mixed with water, are preferred. Plant extracts based on water/propylene glycol at a ratio from 1:10 to 10:1 have proven particularly suitable.

According to the present invention the plant extracts can be used in both pure and diluted form. If they are used in diluted form, they usually contain approx. 2 to 80 wt % active substance, and contain as a solvent the extraction agent or extraction agent mixture used to obtain them.

It may furthermore be preferred to use mixtures of several, in particular two, different plant extracts in the agents according to the present invention.

A number of carboxylic acids are also suitable as a care-providing substance.

Short-chain carboxylic acids can be particularly advantageous for purposes of the invention. "Short-chain" carboxylic acids and derivatives thereof are understood, for purposes of the invention, to be carboxylic acids that can be saturated or unsaturated and/or straight-chain or branched or cyclic and/or aromatic and/or heterocyclic, and have a molecular weight below 750. Saturated or unsaturated straight-chain or branched carboxylic acids having a chain length of 1 to 16 carbon atoms in the chain can be preferred for purposes of the invention; those having a chain length of 1 to 12 carbon atoms in the chain are very particularly preferred.

The short-chain carboxylic acids for purposes of the invention can comprise one, two, three, or more carboxy groups, Carboxylic acids having multiple carboxy groups, in particular di- and tricarboxylic acids, are preferred for purposes of the invention. The carboxy groups can be present entirely or partly as an ester, acid anhydride, lactone, amide, imidic acid, lactam, lactim, dicarboximide, carbohydrazide, hydrazone, hydroxam, hydroxime, amidine, amide oxime, nitrile, or phosphonic or phosphate ester. The carboxylic acids usable according to the present invention can of course be substituted along the carbon chain or the ring structure. Among the substituents of the carboxylic acids usable according to the present invention may be listed, for example, $C_1$ to $C_8$ alkyl, $C_2$ to $C_8$ alkenyl, aryl, aralkyl and aralkenyl, hydroxymethyl, $C_2$ to $C_8$ hydroxyalkyl, $C_2$ to $C_8$ hydroxyalkenyl, aminomethyl, $C_2$ to $C_8$ aminoalkyl, cyano, formyl, oxo, thioxo, hydroxy, mercapto, amino, carboxy or imino groups. Preferred substituents are $C_1$ to $C_8$ alkyl, hydroxymethyl, hydroxy, amino and carboxy groups. Substituents in the α-position are particularly preferred. Very particularly preferred substituents are hydroxy, alkoxy, and amino groups, in which context the amino function can be further substituted, if applicable, with alkyl, aryl, aralkyl, and/or alkenyl radicals. Furthermore, the phosphonic and phosphate esters are likewise preferred carboxylic acid derivatives.

The following may be mentioned as examples of carboxylic acids usable according to the present invention: formic acid, acetic acid, propionic acid, butyric acid, isobutyric acid, valeric acid, isovaleric acid, pivalic acid, oxalic acid, malonic acid, succinic acid, glutaric acid, glyceric acid, glyoxylic acid, adipic acid, pimelic acid, suberic acid, azelaic acid, sebacic acid, propiolic acid, crotonic acid, isocrotonic acid, elaidic acid, maleic acid, fumaric acid, muconic acid, citraconic acid, mesaconic acid, camphoric acid, benzoic acid, o,m,p-phthalic acid, naphthoic acid, toluic acid, hydratropic acid, atropic acid, cinnamic acid, isonicotinic acid, nicotinic acid, bicarbamic acid, 4,4'-dicyano-6,6'-binicotinic acid, 8-carbamoyloctanoic acid, 1,2,4-pentanetricarboxylic acid, 2-pyrrolecarboxylic acid, 1,2,4,6,7-napthalenepentaacetic acid, malonaldehydic acid, 4-hydroxyphthalamidic acid, 1-pyrazolecarboxylic acid, gallic acid, or propanetricarboxylic acid, a dicarboxylic acid selected from the group formed by compounds of the general formula (N-I):

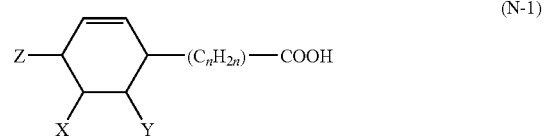

(N-I)

in which Z denotes a linear or branched alkyl or alkenyl group having 4 to 12 carbon atoms, n a number from 4 to 12, and one of the two groups X and Y denotes a COOH group and the other hydrogen or a methyl or ethyl radical, dicarboxylic acids of the general formula (N-I) that additionally bear 1 to 3 methyl or ethyl substituents on the cyclohexene ring, as well as dicarboxylic acids resulting from the dicarboxylic acids according to formula (N-I), in formal terms, by the attachment of one molecule of water to the double bond in the cyclohexene ring.

Dicarboxylic acids of formula (N-I) are known in the literature. A manufacturing method may be inferred, for example, from U.S. Pat. No. 3,753,968.

The dicarboxylic acids of formula (N-I) can be produced, for example, by reacting polyunsaturated dicarboxylic acids with unsaturated monocarboxylic acids in the form of a Diels-Alder cyclization. It is usual to proceed from a polyunsaturated fatty acid as a dicarboxylic acid component. Linoleic acid, accessible from natural fats and oils, is preferred. Acrylic acid in particular, but also e.g. methacrylic acid und crotonic acid, are preferred as a monocarboxylic acid component. Diels-Alder reactions usually result in isomer mixtures in which one component is present in excess. Both these isomer mixtures and the pure compounds can be used according to the present invention.

Also usable, in addition to the preferred dicarboxylic acids according to formula (N-I), are those dicarboxylic acids that differ from the compounds according to formula (N-I) by having 1 to 3 methyl or ethyl substituents on the cyclohexyl ring, or are formed from those compounds in formal terms by the attachment of one molecule of water to the double bond of the cyclohexene ring.

The dicarboxylic acid (mixture) resulting from the reaction of linoleic acid with acrylic acid has proven to be particularly effective according to the present invention. This is a mixture of 5- and 6-carboxy-4-hexyl-2-cyclohexene-1-octanoic acids. Such compounds are commercially available under the designations Westvaco Diacid® 1550 and Westvaco Diacid® 1595 (manufacturer: Westvaco).

In addition to the short-chain carboxylic acids themselves that are listed above by way of example, their physiologically acceptable salts can also be used according to the present invention. Examples of such salts are the alkali, alkaline-earth, and zinc salts, as well as ammonium salts, among which the mono-, di-, and trimethyl-, -ethyl-, and hydroxyethylammonium salts are also to be understood in the context of the present application. Very particularly preferably, however, acids neutralized with alkaline-reacting amino acids, for example arginine, lysine, ornithine, and histidine, can be used in the context of the invention. For formulation reasons, it can also be preferred to select the carboxylic acid from the water-soluble representatives, in particular the water-soluble salts.

It is furthermore preferred according to the present invention to utilize 2-pyrrolidinone-5-carboxylic acid and its derivatives as a carboxylic acid. Particularly preferred are the sodium, potassium, calcium, magnesium or ammonium salts, in which context the ammonium ion carries, in addition to hydrogen, one to three $C_1$ to $C_4$ alkyl groups. The sodium salt is very particularly preferred. The quantities used in the agents according to the present invention are by preference 0.05 to 10 wt % based on the entire application preparation, particularly preferably 0.1 to 5 wt %, and in particular 0.1 to 3 wt %.

It is further preferred according to the present invention to use hydroxycarboxylic acids, and in this context in turn especially the dihydroxy-, trihydroxy- and polyhydroxycarboxylic acids, as well as the dihydroxy-, trihydroxy- and polyhydroxydi-, -tri and -polycarboxylic acid. It has been found in this context that in addition to the hydroxycarboxylic acids, the hydroxycarboxylic acid esters, as well as mixtures of hydroxycarboxylic acids and their esters, and also polymeric hydroxycarboxylic acids and their esters, can be very particularly preferred. Preferred hydroxycarboxylic acid esters are, for example, full esters of glycolic acid, lactic acid, malic acid, tartaric acid, or citric acid. Additional hydroxycarboxylic acid esters that are suitable in principle are esters of β-hydroxypropionic acid, of tartronic acid, of D-gluconic acid, of saccharic acid, of mucic acid, or of glucuronic acid. Suitable as alcohol components of these esters are primary, linear or branched aliphatic alcohols having 8 to 22 carbon atoms, i.e. for example fatty alcohols or synthetic fatty alcohols. The esters of $C_{12}$ to $C_{15}$ fatty alcohols are particularly preferred in this context. Esters of this type are obtainable commercially, e.g. under the trademark Cosmacol® of EniChem, Augusta Industriale. Particularly preferred polyhydroxypolycarboxylic acids are polylactic acid und polytartaric acid as well as esters thereof.

Ectoin or ectoin derivatives, allantoin, taurine, and/or bisabolol are also suitable as a care-providing substance.

The term "ectoin and ectoin derivatives" is understood, according to the present invention, as compounds of formula (IV):

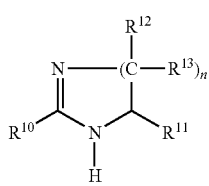
(IVa)

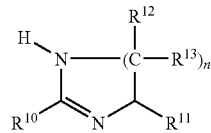
(IVb)

and/or physiologically acceptable salts thereof and/or an isomeric or stereoisomeric form, in which $R^{10}$ denotes a hydrogen atom, a branched or unbranched $C_1$ to $C_4$ alkyl radical, or a $C_2$ to $C_4$ hydroxyalkyl radical;

$R^{11}$ denotes a hydrogen atom, a —$COOR^{14}$ grouping, or a —$CO(NH)R^{14}$ grouping, in which context $R^{14}$ can denote a $C_1$ to $C_4$ alkyl radical, an amino acid radical, or a dipeptide or tripeptide radical;

$R^{12}$ and $R^{13}$ denote, mutually independently, a hydrogen atom, a $C_1$ to $C_4$ alkyl radical, or a hydroxy group, with the stipulation that the two radicals must not simultaneously denote a hydroxy group; and n denotes an integer from 1 to 3.

Suitable physiologically acceptable salts of the general compounds according to formula (IVa) or (IVb) are, for example, the alkaline, alkaline-earth, ammonium, triethylamine, or tris-(2-hydroxyethyl)amine salts, as well as those that result from the reaction of compounds according to formula (IVa) or (IVb) with inorganic and organic acids such as hydrochloric acid, phosphoric acid, sulfuric acid, branched or unbranched, substituted or unsubstituted (for example with one or more hydroxy groups) $C_1$ to $C_4$ mono- or dicarboxylic acids, aromatic carboxylic acids and sulfonic acids such as acetic acid, citric acid, benzoic acid, maleic acid, fumaric acid, tartaric acid, and p-toluenesulfonic acid. Examples of particularly preferred physiologically acceptable salts are the Na, K, Mg, Ca, and ammonium salts of the compounds according to formula (IVa) or (IVb), as well as the salts that result from the reaction of compounds according to formula (IVa) or (IVb) with hydrochloric acid, acetic acid, citric acid, and benzoic acid.

Isomeric or stereoisomeric forms of the compounds according to formula (IVa) or (IVb) are understood, according to the present invention, as all optical isomers, diastereomers, racemates, zwitterions, cations, or mixtures thereof that occur.

The term "amino acid" is understood as the stereoisomeric forms, e.g. D- and L-forms, of the following compounds:
asparagine, arginine, aspartic acid, glutamine, glutamic acid, β-alanine, γ-aminobutyrate, $N_\epsilon$-acetyllysine, $N_\delta$-acetylornithine, $N_\gamma$-acetyldiaminobutyrate, $N_\alpha$-acetyldiaminobutyrate, histidine, isoleucine, leucine, methionine, phenylalanine, serine, threonine and tyrosine.

L-amino acids are preferred. Amino-acid radicals are derived from the corresponding amino acids. The following amino-acid radicals are preferred:
Gly, Ala, Ser, Thr, Val, β-Ala, γ-aminobutyrate, Asp, Glu, Asn, Aln, $N_\epsilon$-acetyllysine, $N_\delta$-acetylornithine, $N_\gamma$-acetyldiaminobutyrate, $N_\alpha$-acetyldiaminobutyrate.

The amino acids have been abbreviated in accordance with generally usual notation. The di- or tripeptide radicals are acid amides in terms of their chemical nature, and decompose into two or three amino acids upon hydrolysis. The amino acids in the di- or tripeptide radical are joined to one another by amide bonds.

With regard to the manufacture of di- and tripeptide radicals, reference is expressly made to EP 0 671 161 A1 of the Marbert company. Examples of di- and tripeptide radicals may also be inferred from the disclosure of EP 0 671 161 A1.

Examples of $C_1$ to $C_4$ alkyl groups in the compounds of formula (IV) are methyl, ethyl, n-propyl, isopropyl, n-butyl, isobutyl and tert.-butyl. Preferred alkyl groups are methyl and ethyl; methyl is a particularly preferred alkyl group. Preferred $C_2$ to $C_4$ hydroxyalkyl groups are the 2-hydroxyethyl, 3-hydroxypropyl or 4-hydroxybutyl groups; 2-hydroxyethyl is a particularly preferred hydroxyalkyl group.

The agents according to the present invention contain these care-providing substances preferably in quantities from 0.001 to 2, in particular from 0.01 to 0.5 wt %, based in each case on the entire application preparation.

Mono- or oligosaccharides can also be used as a care-providing substance in the agents according to the present invention.

Both monosaccharides and oligosaccharides, for example raw sugar, milk sugar, and raffinose, can be used. The use of monosaccharides is preferred according to the present invention. Among the monosaccharides, those compounds containing 5 or 6 carbon atoms are in turn preferred.

Suitable pentoses and hexoses are, for example, ribose, arabinose, xylose, lyxose, allose, altrose, glucose, mannose, gulose, idose, galactose, talose, fucose and fructose. Arabinose, glucose, galactose and fructose are carbohydrates that are preferably used; it is very particularly preferred to use glucose, which is suitable both in the D-(+) or L-(−) configuration or as a racemate.

Derivatives of these pentoses and hexoses, such as the corresponding -onic and -uronic acids (sugar acids), sugar alcohols, and glycosides, can also be used according to the present invention. Preferred sugar acids are gluconic acid, glucuronic acid, saccharic acid, mannosaccharic acid, and mucic acid. Preferred sugar alcohols are sorbitol, mannitol, and dulcitol. Preferred glycosides are the methylglucosides.

Because the mono- or oligosaccharides that are used are usually obtained from natural raw materials such as starch, in general they exhibit the configurations corresponding to those raw materials (e.g. D-glucose, D-fructose and D-galactose).

The mono- or oligosaccharides are contained in the agents according to the present invention preferably in a quantity from 0.1 to 8 wt %, particularly preferably from 1 to 5 wt %, based on the entire application preparation.

The agent can furthermore contain at least one lipid as a care-providing substance.

Lipids suitable according to the present invention are phospholipids, for example soy lecithin, egg lecithin, and kephalins, as well as the substances known by the INCI names Linoleamidopropyl PG-Dimonium Chloride Phosphate, Cocamidopropyl PG-Dimonium Chloride Phosphate, and Stearamidopropyl PG-Dimonium Chloride Phosphate. These are marketed, for example, by the Mona company under the commercial designations Phospholipid EFA®, Phospholipid PTC®, and Phospholipid SV®.

The agents according to the present invention contain the lipids preferably in quantities from 0.01 to 10 wt %, in particular 0.1 to 5 wt %, based on the entire application preparation.

Oily substances are also suitable as a care-providing substance.

Among the natural and synthetic cosmetic oily substances may be listed, for example:

Vegetable oils. Examples of such oils are sunflower oil, olive oil, soybean oil, rapeseed oil, almond oil, jojoba oil, orange oil, wheat germ oil, peach-kernel oil, and the liquid components of coconut oil. Also suitable, however, are other triglyceride oils such as the liquid components of beef tallow, as well as synthetic triglyceride oils.

Liquid paraffin oils, isoparaffin oils, and synthetic hydrocarbons, as well as di-n-alkyl ethers having a total of between 12 and 36 carbon atoms, in particular 12 to 24 carbon atoms, such as, for example, di-n-octyl ether, di-n-decyl ether, di-n-nonyl ether, di-n-undecyl ether, di-n-dodecyl ether, n-hexyl-n-octyl ether, n-octyl-n-decyl ether, n-decyl-n-undecyl ether, n-undecyl-n-dodecyl ether, and n-hexyl-n-undecyl ether, as well as ditert.-butyl ether, diisopentyl ether, di-3-ethyldecyl ether, tert.-butyl-n-octyl ether, isopentyl-n-octyl ether, and 2-methylpentyl-n-octyl ether The compounds 1,3-di-(2-ethylhexyl)cyclohexane (Cetiol® S) and di-n-octyl ether (Cetiol® OE), available as commercial products, can be preferred.

Ester oils. "Ester oils" are to be understood as the esters of $C_6$ to $C_{30}$ fatty acids with $C_2$ to $C_{30}$ fatty alcohols. The monoesters of fatty acids with alcohols having 2 to 24 carbon atoms are preferred. Examples of fatty acid components used in the esters are hexanoic acid, octanoic acid, 2-ethylhexanoic acid, decanoic acid, lauric acid, isotridecanoic acid, myristic acid, palmitic acid, palmitoleic acid, stearic acid, isostearic acid, oleic acid, elaidic acid, petroselinic acid, linoleic acid, linolenic acid, eleostearic acid, arachidic acid, gadoleic acid, behenic acid, and erucic acid, as well as industrial mixtures thereof that occur, for example, upon high-pressure cleavage of natural fats and oils, upon oxidation of aldehydes from Roelen oxosynthesis, or upon dimerization of unsaturated fatty acids. Examples of the fatty alcohol components in the ester oils are isopropyl alcohol, hexanol, octanol, 2-ethylhexyl alcohol, decanol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol, and brassidyl alcohol, as well as industrial mixtures thereof that occur, for example, upon high-pressure hydrogenation of industrial methyl esters based on fats and oils or aldehydes from Roelen oxosynthesis, and as a monomer fraction upon dimerization of unsaturated fatty alcohols. Particularly preferred according to the present invention are isopropyl myristate (Rilanit® IPM), isononanoic acid $C_{16-18}$ alkyl ester (Cetiol® SN), 2-ethylhexyl palmitate (Cegesoft® 24), stearic acid 2-ethylhexyl ester (Cetiol® 868), cetyl oleate, glycerol tricaprylate, coconut fatty alcohol caprinate/caprylate (Cetiol® LC), n-butyl stearate, oleyl erucate (Cetiol® J 600), isopropyl palmitate (Rilanit® IPP), Oleyl Oleate (Cetiol®), lauric acid hexyl ester (Cetiol® A), di-n-butyl adipate (Cetiol® B), myristyl myristate (Cetiol® MM), Cetearyl Isononanoate (Cetiol® SN), oleic acid decyl ester (Cetiol® V).

Dicarboxylic acid esters such as di-n-butyl adipate, di(2-ethylhexyl) adipate, di(2-ethylhexyl) succinate, and diisotridecyl acelaate, as well as diol esters such as ethylene glycol dioleate, ethylene glycol diisotridecanoate, propylene glycol di(2-ethyl hexanoate), propylene glycol diisostearate, propylene glycol dipelargonate, butanediol diisostearate, neopentyl glycol dicaprylate.

Symmetrical, asymmetrical, or cyclic esters of carbonic acid with fatty alcohols, described for example in German Application DE 197 56 454, glycerol carbonate, or dicaprylyl carbonate (Cetiol® CC).

Fatty acid triesters of saturated and/or unsaturated linear and/or branched fatty acids with glycerol.

Fatty acid partial glycerides, i.e. monoglycerides, diglycerides, and industrial mixtures thereof. When industrial products are used, small quantities of triglycerides can still be present for manufacturing-related reasons. The partial glycerides preferably conform to formula (D4-I):

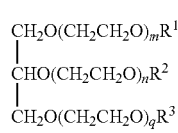

(D4-I)

in which $R^1$, $R^2$ and $R^3$, mutually independently, denote hydrogen or a linear or branched, saturated and/or unsaturated acyl radical having 6 to 22, preferably 12 to 18, carbon atoms, with the stipulation that at least one of these groups denotes an acyl radical and at least one of these groups denotes hydrogen. The sum (m+n+q) denotes 0 or numbers from 1 to 100, preferably 0 or 5 to 25. $R^1$ preferably denotes an acyl radical and $R^2$ and $R^3$ denote hydrogen, and the sum (m+n+q) is 0. Typical examples are mono- and/or diglycerides based on hexanoic acid, octanoic acid, 2-ethylhexanoic acid, decanoic acid, lauric acid, isotridecanoic acid, myristic acid, palmitic acid, palmoleic acid, stearic acid, isostearic acid, oleic acid, elaidic acid, petroselinic acid, linoleic acid, linolenic acid, eleostearic acid, arachidic acid, gadoleic acid, behenic acid and erucic acid, as well as industrial mixtures thereof. Oleic acid monoglycerides are preferably used.

The quantity of the natural and synthetic cosmetic oily substances used in the agents according to the present invention is usually 0.1 to 30 wt % based on the entire application preparation, preferably 0.1 to 20 wt %, and in particular 0.1 to 15 wt %.

The agent can furthermore contain an enzyme as a care-providing substance, Enzymes particularly preferred according to the present invention are selected from a group made up of proteases, lipases, transglutaminase, oxidases and peroxidases.

Pearl extracts are also suitable as a care-providing substance,

Mussel pearls are made up substantially of inorganic and organic calcium salts, trace elements, and proteins. Pearls can easily be obtained from cultivated mussels. Mussel cultivation can be accomplished in both fresh water and seawater; this can have an effect on the constituents of the pearls. A pearl extract that derives from mussels cultivated in seawater or salt water is preferred according to the present invention. The pearls are made up largely of aragonite (calcium carbonate), conchiolin, and an albuminoid; the latter constituents are proteins. Also contained in pearls are magnesium and sodium salts, inorganic silicon compounds, and phosphates.

The pearls are powdered for production of the pearl extract. The powdered pearls are then extracted with the usual methods. Water, alcohols, and mixtures thereof can be used as extraction agents for production of the pearl extracts. "Water" is to be understood in this context as both demineralized water and seawater. Among the alcohols, lower alcohols such as ethanol and isopropanol, but in particular polyvalent alcohols such as glycerol, diglycerol, triglycerol, polyglycerol, ethylene glycol, propylene glycol, and butylene glycol, are preferred, both as a sole extraction agent and also mixed with demineralized water or seawater. Pearl extracts based on water/glycerol mixtures have proven to be particularly suitable. Depending on the extraction conditions, the pearl proteins (conchiolin and albuminoid) can be present to a very large extent in the natural state, or already partly or very largely as protein hydrolysates. A pearl extract in which conchiolin and albuminoid are already present in partly hydrolyzed fashion is preferred. The essential amino acids of these proteins are glutamic acid, serine, alanine, glycine, aspartic acid, and phenylalanine. In a further particularly preferred embodiment, it can be advantageous if the pearl extract is additionally enriched with at least one or more of these amino acids. In the most preferred embodiment, the pearl extract is enriched with glutamic acid, serine, and leucine. In addition, depending on the extraction conditions, in particular as a function of the extraction agent selected, a greater or lesser proportion of minerals and trace elements may still be present in the extract. A preferred extract contains organic and/or inorganic calcium salts as well as magnesium and sodium salts, inorganic silicon compounds, and/or phosphates. A very particularly preferred pearl extract contains at least 75%, preferably 85%, particularly preferably 90%, and very particularly preferably 95% of all the constituents of the naturally occurring pearls. Examples of pearl extracts usable according to the present invention are the commercial products Pearl Protein Extract BG® or Crodarom® Pearl.

The pearl extracts described above are contained by preference in a quantity from at least 0.01 to 20 wt %. The quantities of the extract used are preferably from 0.01 to 10 wt %, very particularly preferably 0.01 to 5 wt %, based on the entire application preparation.

Although each of the aforesaid care-providing substances already yields a satisfactory result of itself, all embodiments in which the agent contains multiple care-providing substances, including from different groups, are also encompassed within the scope of the present invention.

The addition of a UV filter allows both the agents themselves, and the treated skin or hair, to be protected from damaging influences of UV radiation. At least one UV filter is therefore by preference added to the agent. The UV filters suitable according to the present invention are not subject to any general restrictions in terms of their structure and their physical properties. Instead, all UV filters usable in the cosmetics sector, whose absorption maximum lies in the UVA (315-400 nm) UVB (280-315 nm), or UVC (<280 nm) regions, are suitable. UV filters having an absorption maximum in the UVB region, in particular in the region from approximately 280 to approximately 300 nm, are particularly preferred.

The UV filters preferred according to the present invention can be selected, for example, from substituted benzophenones, p-aminobenzoic acid esters, diphenylacrylic acid esters, cinnamic acid esters, salicylic acid esters, benzimidazoles, and o-aminobenzoic acid esters.

Examples of UV filters usable according to the present invention are 4-aminobenzoic acid, N,N,N-trimethyl-4-(2-oxoborn-3-ylidene methyl)aniline methylsulfate, 3,3,5-trimethylcyclohexyl salicylate (Homosalate), 2-hydroxy-4-methoxybenzophenone (Benzophenone-3; Uvinul® M 40, Uvasorb® MET, Neo Heliopan® BB, Eusolex® 4360), 2-phenylbenzimidazole-5-sulfonic acid and its potassium, sodium, and triethanolamine salts (phenylbenzimidazole-sulfonic acid; Parsol® HS; Neo Heliopan® Hydro), 3,3'-(1,4-phenylenedimethylene)-bis(7,7-dimethyl-2-oxo-bicyclo-[2.2.1]hept-1-yl-methanesulfonic acid) and its salts, 1-(4-tert.-butylphenyl)-3-(4-methoxyphenyl)propane-1,3-dione (butylmethoxydibenzoylmethane; Parsol® 1789, Eusolex® 9020), α-(2-oxoborn-3-ylidene)toluene-4-sulfonic acid and its salts, ethoxylated 4-aminobenzoic acid ethyl ester (PEG- 25 PABA; Uvinuil® P 25), 4-dimethylaminobenzoic acid 2-ethylhexyl ester (Octyl Dimethyl PABA; Uvasorb® DMO, Escalol® 507, Eusolex® 6007), salicylic acid 2-ethylhexyl ester (Octyl Salicylate; Escalol® 587, Neo Heliopan® OS, Uvinul® 018), 4-methoxycinnamic acid isopentyl ester (Isoamyl p-Methoxycinnamate; Neo Heliopan® E 1000), 4-methoxycinnamic acid 2-ethylhexyl ester (Octyl Methoxycinnamate; Parsol® MCX, Escalo® 557, Neo Heliopan® AV), 2-hydroxy-4-methoxybenzophenone-5-sulfonic acid and its sodium salt (Benzophenone-4, Uvinul® MS 40; Uvasorb® S 5), 3-(4'-methylbenzylidene) D,L-camphor(4-Methylbenzylidene Camphor; Parsol® 5000, Eusolex® 6300), 3-benzylidene camphor (3-Benzylidene Camphor), 4-isopropylbenzylsalicylate, 2,4,6-trianilino-(p-carbo-2'-ethylhexyl-1'-oxi)-1,3,5-triazine, 3-imidazol-4-ylacrylic acid and its ethyl esters, polymers of N-{(2 and 4)-[2-oxoborn-3-ylidenemethyl]benzyl}acrylamide, 2,4-dihydroxybenzophenone (Benzophenone-1; Uvasorb® 20 H, Uvinul® 400), 1,1'-diphenylacrylonitrilic acid 2-ethylhexyl ester (Octocrylene; Eusolex® OCR, Neo Heliopan® Type 303, Uvinul® N 539 SG), o-aminobenzoic acid menthyl ester (Menthyl Anthranilate; Neo Heliopan® MA), 2,2',4,4'-tetrahydroxybenzophenone (Benzophenone-2; Uvinul® D-50), 2,2'-dihydroxy-4,4'-dimethoxybenzophenone (Benzophenone-6), 2,2'-dihydroxy-4,4'-dimethoxybenzophenone-5-sodiumsulfonate, and 2-cyano-3,3-diphenylacrylic acid 2'-ethylhexyl ester. 4-Aminobenzoic acid, N,N,N-trimethyl-4-(2-oxoborn-3-ylidene methyl)aniline methylsulfate, 3,3,5-trimethylcyclohexyl salicylate, 2-hydroxy-4-methoxybenzophenone, 2-phenylbenzimidazole-5-sulfonic acid and its potassium, sodium, and triethanolamine salts, 3,3'-(1,4-phenylenedimethylene)-bis(7,7-dimethyl-2-oxo-bicyclo-[2.2.1]hept-1-yl-methanesulfonic acid) and its salts, 1-(4-tert.-butylphenyl)-3-(4-methoxyphenyl)propane-1,3-dione, α-(2-oxoborn-3-ylidene)toluene-4-sulfonic acid and its salts, ethoxylated 4-aminobenzoic acid ethyl ester, 4-dimethylaminobenzoic acid 2-ethylhexyl ester, salicylic acid 2-ethylhexyl ester, 4-methoxycinnamic acid isopentyl ester, 4-methoxycinnamic acid 2-ethylhexyl ester, 2-hydroxy-4-methoxybenzophenone-5-sulfonic acid and its sodium salt, 3-(4'-methylbenzylidene)-D,L-camphor, 3-benzylidene camphor, 4-isopropylbenzyl salicylate, 2,4,6-trianilino-(p-carbo-2'-ethylhexyl-1'-oxi)-1,3,5-triazine, 3-imidazol-4-ylacrylic acid and its ethyl esters, and polymers of N-{(2 and 4)-[2-oxoborn-3-ylidenemethyl]benzyl}acrylamide are preferred. Very particularly preferred according to the present invention are 2-hydroxy-4-methoxybenzophenone, 2-phenylbenzimidazole-5-sulfonic acid and its potassium, sodium, and triethanolamine salts, 1-(4-tert.-butylphenyl)-3-(4-methoxyphenyl)propane-1,3-dione, 4-methoxycinnamic acid 2-ethylhexyl ester, and 3-(4'-methylbenzylidene)D, L-camphor.

Those UV filters whose molar extinction coefficient at the absorption maximum is above 15,000, in particular above 20,000, are preferred.

It has furthermore been found that with structurally similar UV filters, in the context of the teaching of the present invention the water-insoluble compound in many cases exhibits the greater effectiveness as compared with water-soluble compounds of this kind that differ from it by having one or more additionally ionic groups. In the context of the invention, those UV filters of which no more than 1 wt %, in particular no more than 0.1 wt %, dissolves in water at 20° C., are understood to be water-insoluble. These compounds should furthermore be soluble at a proportion of at least 0.1 wt %, in particular at least 1 wt %, in common cosmetic oil components at room temperature. The use of water-insoluble UV filters can therefore be preferred according to the present invention.

According to a further embodiment of the present invention, those UV filters that comprise a cationic group, in particular a quaternary ammonium group, are preferred.

These UV filters exhibit the general structure U-Q.

The structural part U denotes a group that absorbs UV radiation. This group can in principle be derived from the aforementioned known UV filters usable in the cosmetics sector, in which one group, generally a hydrogen atom, of the UV filter is replaced by a cationic group Q, in particular by a quaternary amino function.

Compounds from which structural part U can be derived are, for example
 substituted benzophenones;
 p-aminobenzoic acid esters;
 diphenylacrylic acid esters;
 cinnamic acid esters;
 salicylic acid esters;
 benzimidazoles; and
 o-aminobenzoic acid esters.

Structural parts U that are derived from cinnamic acid amide or from N,N-dimethylaminobenzoic acid amide are preferred according to the present invention.

Structural parts U can in principle be selected so that the absorption maximum of the UV filters can lie both in the UVA (315-400 nm) region and in the UVB (280-315 nm) region, or in the UVC (<280 nm) region. UV filters having an absorption maximum in the UVB region, in particular in the region from approximately 280 to approximately 300 nm, are particularly preferred.

Structural part U is furthermore preferably selected, including as a function of structural part Q, in such a way that the molar extinction coefficient of the UV filter at the absorption maximum is above 15,000, in particular above 20,000.

Structural part Q preferably contains a quaternary ammonium group as a cationic group. This quaternary ammonium group can in principle be connected directly to structural part U, so that structural part U represents one of the four substituents of the positively charged nitrogen atom. Preferably, however, one of the four substituents on the positively charged nitrogen atom is a group, in particular an alkylene group, having 2 to 6 carbon atoms, that functions as a connection between structural part U and the positively charged nitrogen atom.

Advantageously, the group Q has the general structure —$(CH_2)_x$—$N^+R^1R^2R^3X^-$, in which x denotes an integer from 1 to 4, $R^1$ and $R^2$, mutually independently, denote $C_{1-4}$ alkyl groups, $R^3$ denotes a $C_{1-22}$ alkyl group or a benzyl group, and X— denotes a physiologically acceptable anion. In the context of this general structure, x preferably denotes the number 3, $R^1$ and $R^2$ each denote a methyl group, and $R^3$ denotes either a methyl group or a saturated or unsaturated, linear or branched hydrocarbon chain having 8 to 22, in particular 10 to 18, carbon atoms.

Physiologically acceptable anions are, for example, inorganic anions such as halides, in particular chloride, bromide and fluoride, sulfate ions, and phosphate ions, as well as organic anions such as lactate, citrate, acetate, tartrate, methosulfate, and tosylate.

Two preferred UV filters having cationic groups are the compounds cinnamic acid amidopropyltrimethylammonium chloride (Incroquat® UV-283) and dodecyldimethylaminobenzamidopropyldimethylammonium tosylate (Escalol® HP 610), available as commercial products.

The teaching of the present invention of course also encompasses the use of a combination of several UV filters. In the context of this embodiment, the combination of at least one water-insoluble UV filter with at least one UV filter having a cationic group is preferred.

The UV filters are contained usually in quantities from 0.01 to 5 wt % based on the entire application preparation. Quantities from 0.1 to 2.5 wt % are preferred.

Depending on the nature of the agent according to the present invention, it may furthermore need to contain at least one surfactant. This applies in particular to skin cleaning agents and shampoos. Other agents as well, however, for example hair rinses, hair therapies, and certain styling agents, in particular styling foams, can contain surfactants.

Cationic surfactants, for example, which have already been described above as suitable care-providing substances, can be used. The statements made above apply correspondingly with regard to the preferred cationic surfactants and the quantities used.

In addition to or instead of the cationic surfactants, the agents can contain further surfactants or emulsifiers, both anionic as well as ampholytic and nonionic surfactants, and all types of known emulsifiers, being suitable in principle. The group of the ampholytic or also amphoteric surfactants encompasses zwitterionic surfactants and ampholytes. The surfactants can already have an emulsifying effect.

All anionic surface-active substances suitable for use on the human body are, in principle, appropriate as anionic surfactants. These are characterized by an anionic group imparting water solubility, for example a carboxylate, sulfate, sulfonate, or phosphate group, and a lipophilic alkyl group having approximately 8 to 30 carbon atoms. Glycol or polyglycol ether groups, ester, ether, and amide groups, and hydroxyl groups can additionally be contained in the molecule. Examples of suitable anionic surfactants are, in each case in the form of the sodium, potassium, and ammonium and mono-, di-, and trialkanolammonium salts having 2 to 4 carbon atoms in the alkanol group:

linear and branched fatty acids having 8 to 30 carbon atoms (soaps);
ethercarboxylic acids of the formula R—O—($CH_2$—$CH_2O$)$_x$—$CH_2$—COOH, in which R is a linear alkyl group having 8 to 30 carbon atoms and x=0 or is 1 to 16;
acyl sarcosides having 8 to 24 carbon atoms in the acyl group;
acyl taurides having 8 to 24 carbon atoms in the acyl group;
acyl isethionates having 8 to 24 carbon atoms in the acyl group;
sulfosuccinic acid mono- and dialkyl esters having 8 to 24 carbon atoms in the alkyl group, and sulfosuccinic acid monoalkylpolyoxyethyl esters having 8 to 24 carbon atoms in the alkyl group and 1 to 6 oxyethyl groups;
linear alkanesulfonates having 8 to 24 carbon atoms;
linear alpha-olefinsulfonates having 8 to 24 carbon atoms;
alpha-sulfo fatty acid methyl esters of fatty acids having 8 to 30 carbon atoms;
alkyl sulfates and alkyl polyglycol ether sulfates of the formula R—O—($CH_2$—$CH_2$—O)$_x$—$OSO_3H$, in which R is a preferably linear alkyl group having 8 to 30 carbon atoms and x=0 or 1 to 12;
mixtures of surface-active hydroxysulfonates;
sulfated hydroxyalkylpolyethylene and/or hydroxyalkylenepropylene glycol ethers;
sulfonates of unsaturated fatty acids having 8 to 24 carbon atoms and 1 to 6 double bonds;
esters of tartaric acid and citric acid with alcohols, representing addition products of approximately 2 to 15 molecules of ethylene oxide and/or propylene oxide with fatty alcohols having 8 to 22 carbon atoms;
alkyl and/or alkenyl ether phosphates of formula (E1-I):

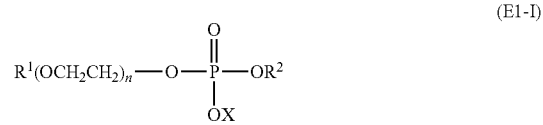

(E1-I)

in which $R^1$ preferably denotes an aliphatic hydrocarbon radical having 8 to 30 carbon atoms, $R^2$ denotes hydrogen, a $(CH_2CH_2O)_nR^1$ radical, or X, n denotes numbers from 1 to 10, and X denotes hydrogen, an alkaline or alkaline-earth metal, or $NR^3R^4R^5R^6$, where $R^3$ to $R^6$, mutually independently, denote hydrogen or a $C_1$ to $C_4$ hydrocarbon radical;
sulfated fatty acid alkylene glycol esters of formula (E1-II):

$R^7CO(AlkO)_nSO_3M$ (E1-II)

in which $R^7CO$ denotes a linear or branched, aliphatic, saturated and/or unsaturated acyl radical having 6 to 22 carbon atoms, Alk denotes $CH_2CH_2$, $CHCH_3CH_2$, and/or $CH_2CHCH_3$, n denotes numbers from 0.5 to 5, and M denotes a cation such as those described in German Application 197 36 906;
monoglyceride sulfates and monoglyceride ether sulfates of formula (E1-III):

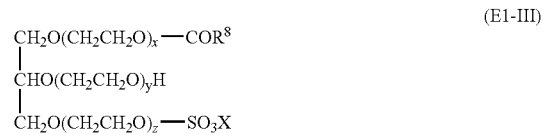

(E1-III)

in which $R^8CO$ denotes a linear or branched acyl radical having 6 to 22 carbon atoms, x, y, and z in total denote 0 or numbers from 1 to 30, preferably 2 to 10 and X denotes an alkali or alkaline-earth metal. Typical examples of monoglyceride (ether) sulfates suitable for purposes of the invention are the reaction products of lauric acid monoglyceride, coconut fatty acid monoglyceride, palmitic acid monoglyceride, stearic acid monoglyceride, oleic acid monoglyceride, and tallow fatty acid monoglyceride, as well as their ethylene oxide adducts with sulfur trioxide or chlorosulfonic acid in the form of their sodium salts. Monoglyceride sulfates of formula (E1-III) in which $R^8CO$ denotes a linear acyl radical having 8 to 18 carbon atoms are used by preference;
amide ethercarboxylic acids;
condensation products of $C_8$ to $C_{30}$ fatty alcohols with protein hydrolysates and/or amino acids and their derivatives, known to one skilled in the art as protein fatty acid condensates, such as, for example, Lamepon® grades, Gluadin® grades, Hostapon® KCG, or the Amisoft® grades.

Preferred anionic surfactants are alkyl sulfates, alkyl polyglycol ether sulfates, and ethercarboxylic acids having 10 to 18 carbon atoms in the alkyl group and up to 12 glycol ether groups in the molecule, sulfosuccinic acid mono- and dialkyl esters having 8 to 18 carbon atoms in the alkyl group, and sulfosuccinic acid monoalkylpolyoxyethyl esters having 8 to 18 carbon atoms in the alkyl group and 1 to 6 oxyethyl groups, monoglycerol disulfates, alkyl and alkenyl ether phosphates, and protein fatty acid condensates.

"Zwitterionic surfactants" refers to those surface-active compounds that contain in the molecule at least one quaternary ammonium group and at least one —COO$^{(-)}$ or —SO$_3^{(-)}$ group. Particularly suitable zwitterionic surfactants are the so-called betaines, such as the N-alkyl-N,N-dimethylammonium glycinates, for example cocalkyldimethylammonium glycinate, N-acylaminopropyl-N,N-dimethylammonium glycinates, for example cocacylaminopropyldimethylammonium glycinate, and 2-alkyl-3-carboxymethyl-3-hydroxyethylimidazolines, having in each case 8 to 18 carbon atoms in the alkyl or acyl group, as well as cocacylaminoethylhydroxyethylcarboxymethyl glycinate. A preferred zwitterionic surfactant is the fatty acid amide derivative known by the INCI name Cocamidopropyl Betaine.

"Ampholytes" are understood to be those surface-active compounds that contain in the molecule, in addition to a $C_8$ to $C_{24}$ alkyl or acyl group, at least one free amino group and at least one —COOH or —SO$_3$H group, and are capable of forming internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids, and alkylaminoacetic acids, having in each case approximately 8 to 24 carbon atoms in the alkyl group. Particularly preferred ampholytes are N-cocalkylaminopropionate, cocacylaminoethylaminopropionate, and $C_{12-18}$ acyl sarcosine.

Nonionic surfactants contain as a hydrophilic group, for example, a polyol group, a polyalkylene glycol ether group, or a combination of a polyol and polyglycol ether group. Such compounds are, for example:
addition products of 2 to 50 mol ethylene oxide and/or 1 to 5 mol propylene oxide with linear and branched fatty alcohols having 8 to 30 carbon atoms, with fatty acids having 8 to 30 carbon atoms, and with alkylphenols having 8 to 15 carbon atoms in the alkyl group;
addition products, end-capped with a methyl or $C_2$ to $C_6$ alkyl group, of 2 to 50 mol ethylene oxide and/or 1 to 5 mol propylene oxide with linear and branched fatty alcohols having 8 to 30 carbon atoms, with fatty acids having 8 to 30 carbon atoms, and with alkylphenols having 8 to 15 carbon atoms in the alkyl group, such as, for example, the grades obtainable under the marketing designations Dehydrol® LS, Dehydrol® LT (Cognis);
$C_{12}$ to $C_{30}$ fatty acid mono- and diesters of addition products of 1 to 30 mol ethylene oxide with glycerol;
addition products of 5 to 60 mol ethylene oxide with castor oil and hardened castor oil;
polyol fatty acid esters such as, for example, the commercial product Hydagen® HSP (Cognis), or Sovermol grades (Cognis);
alkoxylated triglycerides;
alkoxylated fatty acid alkyl esters of formula (E4-I):

$$R^1CO-(OCH_2CHR^2)_wOR^3 \quad (E4\text{-}I),$$

in which $R^1CO$ denotes a linear or branched, saturated and/or unsaturated acyl radical having 6 to 22 carbon atoms, $R^2$ denotes hydrogen or methyl, $R^3$ denotes linear or branched alkyl radicals having 1 to 4 carbon atoms, and w denotes numbers from 1 to 20;
amine oxides;
hydroxy mixed ethers, such as those described e.g. in German Application 197 38 866;
sorbitan fatty acid esters and addition products of ethylene oxide with sorbitan fatty acid esters, for example the polysorbates;
sugar fatty acid esters and addition products of ethylene oxide with sugar fatty acid esters;
addition products of ethylene oxide with fatty acid alkanolamides and fatty amines;
sugar surfactants of the alkyl and alkenyl oligoglycoside types, according to formula (E4-II)

in which $R^4$ denotes an alkyl or alkenyl radical having 4 to 22 carbon atoms, G denotes a sugar radical having 5 or 6 carbon atoms, and p denotes numbers from 1 to 10. They can be obtained in accordance with the relevant methods of preparative organic chemistry.

The alkyl and alkenyl oligoglycosides can be derived from aldoses or ketoses having 5 or 6 carbon atoms, preferably from glucose. The preferred alkyl or alkenyl oligoglycosides are thus alkyl and/or alkenyloligoglucosides. The index number p in the general formula (E4-II) indicates the degree of oligomerization (DP), i.e. the distribution of mono- and oligoglycosides, and denotes a number between 1 and 10. Whereas p in the individual molecule must always be integral, and here can principally assume the values p=1 to 6, the value p for a specific alkyl oligoglycoside is an analytically ascertained calculated value, which usually represents a fractional number. Alkyl and/or alkenyl oligoglycosides having an average degree of oligomerization p from 1.1 to 3.0 are preferably used. In terms of applications engineering, those alkyl and/or alkenyl oligoglycosides whose degree of oligomerization is less than 1.7, and in particular between 1.2 and 1.4, are preferred. The alkyl or alkenyl radical $R^4$ can be derived from primary alcohols having 4 to 11, preferably 8 to 10 carbon atoms. Typical examples are butanol, hexanol, octanol, decanol, and undecyl alcohol as well as industrial mixtures thereof, such as those obtained, for example, upon hydrogenation of industrial fatty acid methyl esters or in the course of the hydrogenation of aldehydes from Roelen oxosynthesis. Preferred are alkyl oligoglucosides of chain length $C_8$ to $C_{10}$ (DP=1 to 3), which occur as the first runnings upon distillational separation of industrial $C_8$ to $C_{18}$ coconut oil alcohol and can be contaminated with a proportion of less than 6 wt % $C_{12}$ alcohol, and alkyl oligoglucosides based on industrial $C_{9/11}$ oxoalcohols (DP=1 to 3). The alkyl or alkenyl radical $R^{15}$ can furthermore also be derived from primary alcohols having 12 to 22, preferably 12 to 14 carbon atoms. Typical examples are lauryl alcohol, myristyl alcohol, cetyl alcohol, palmoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol and industrial mixtures thereof, which can be obtained as described above. Alkyl oligoglucosides based on hardened $C_{12/14}$ cocalcohol having a DP of 1 to 3 are preferred.
sugar surfactants of the type of the fatty acid N-alkylpolyhydroxyalkylamides, a nonionic surfactant of the formula (E4-III)

in which $R^5CO$ denotes an aliphatic acyl radical having 6 to 22 carbon atoms, $R^6$ denotes hydrogen, an alkyl or hydroxyalkyl radical having 1 to 4 carbon atoms, and [Z] denotes a linear or branched polyhydroxyalkyl radical having 3 to 12 carbon atoms and 3 to 10 hydroxyl groups. The fatty acid N-alkylpolyhydroxyalkylamides are known substances that can usually be obtained by reductive amination of a reducing sugar with ammonia, an alkylamine, or an alkanolamine, and subsequent acylation with a fatty acid, a fatty acid alkyl ester, or a fatty acid chloride. The fatty acid N-alkylpolyhydroxyalkylamides are preferably derived from reducing sugars having 5 or 6 carbon atoms, in particular from glucose. The preferred fatty acid N-alkylpolyhydroxyalkylamides therefore represent fatty acid N-alkylglucamides such as those reproduced by the formula (E4-IV):

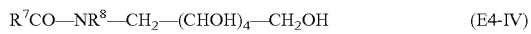

$$R^7CO—NR^8—CH_2—(CHOH)_4—CH_2OH \quad (E4\text{-}IV)$$

It is preferable to use, as fatty acid N-alkylpolyhydroxyalkylamides, glucamides of the formula (E4-IV) in which $R^8$ denotes hydrogen or an alkyl group, and $R^7CO$ denotes the alkyl radical of hexanoic acid, octanoic acid, decanoic acid, lauric acid, myristic acid, palmitic acid, palmoleic acid, stearic acid, isostearic acid, oleic acid, elaidic acid, petroselinic acid, linoleic acid, linolenic acid, arachidic acid, gadoleic acid, behenic acid, erucic acid, or industrial mixtures of those acids. Particularly preferred are fatty acid N-alkylglucamides of formula (E4-IV) that are obtained by reductive amination of glucose with methylamine and subsequent acylation with lauric acid or $C_{12/14}$ coconut fatty acid, or a corresponding derivative. The polyhydroxyalkylamides can furthermore also be derived from maltose and palatinose.

The alkylene oxide addition products with saturated linear fatty alcohols and fatty acids, having respectively 2 to 30 mol ethylene oxide per mol fatty alcohol or fatty acid, have proven to be preferred further nonionic surfactants. Preparations having outstanding properties are likewise obtained if they contain, as nonionic surfactants, fatty acid esters of ethoxylated glycerol.

These compounds are characterized by the following parameters: The alkyl radical R contains 6 to 22 carbon atoms and can be both linear and branched. Primary linear aliphatic radicals, and those methyl-branched in the 2-position, are preferred. Such alkyl radicals are, for example, 1-octyl, 1-decyl, 1-lauryl, 1-myristyl, 1-cetyl, and 1-stearyl. 1-Octyl, 1-decyl, 1-lauryl, and 1-myristyl are particularly preferred. When so-called "oxo alcohols" are used as the initial materials, compounds having an odd number of carbon atoms in the alkyl chain predominate.

The sugar surfactants can also be contained as nonionic surfactants. These can be contained preferably in quantities from 0.1 to 20 wt %, based on the respective entire composition. Quantities from 0.5 to 15 wt % are particularly preferred, and quantities from 0.5 to 7.5 wt % are very particularly preferred.

The compounds having alkyl groups used as surfactants can in each case be uniform substances. It is generally preferred, however, to proceed from natural vegetable or animal raw materials when producing these substances, so that substance mixtures having different alkyl chain lengths, dependent on the particular material, are obtained.

In the surfactants that represent addition products of ethylene oxide and/or propylene oxide with fatty alcohols, or derivatives of such addition products, both products having a "normal" homolog distribution and those having a restricted homolog distribution can be used. A "normal" homolog distribution is understood as mixtures of homologs that are obtained when reacting fatty alcohol and alkylene oxide using alkali metals, alkali-metal hydroxides, or alkali-metal alcoholates as catalysts. Restricted homolog distributions, on the other hand, are obtained when, for example, hydrotalcites, alkaline-earth metal salts of ethercarboxylic acids, or alkaline-earth metal oxides, hydroxides, or alcoholates are used as catalysts. The use of products having a restricted homolog distribution can be preferred.

The further surfactants are used as a rule in quantities from 0.1 to 45 wt %, preferably 0.5 to 30 wt %, and very particularly preferably from 0.5 to 25 wt %, based on the respective entire composition. The quantity used depends substantially on the purpose being fulfilled by the agent according to the present invention. In the case of a shampoo or another cleaning agent, surfactant quantities above 45 wt % are also usual.

The agents can furthermore contain at least one emulsifier. Emulsifiers cause the formation, at the phase interface, of water- or oil-stable adsorption layers that prevent the dispersed droplets from coalescing, and thereby stabilize the emulsion. Emulsions are therefore, like surfactants, constructed from a hydrophobic and a hydrophilic molecule. Hydrophilic emulsifiers preferentially form O/W emulsions, and hydrophobic emulsifiers preferentially form W/O emulsions. Selection of these emulsifying surfactants or emulsifiers is based on the substances to be dispersed and the respective external phase, and on the fineness of the emulsion particles. Emulsifiers usable according to the present invention are, for example:

- addition products of 4 to 100 mol ethylene oxide and/or 1 to 5 mol propylene oxide with linear fatty alcohols having 8 to 22 carbon atoms, with fatty acids having 12 to 22 carbon atoms, and with alkylphenols having 8 to 15 carbon atoms in the alkyl group;
- $C_{12}$ to $C_{22}$ fatty acid mono- and diesters of addition products of 1 to 30 mol ethylene oxide with polyols having 3 to 6 carbon atoms, in particular with glycerol;
- addition products of ethylene oxide and polyglycerol with methyl glucoside fatty acid esters, fatty acid alkanolamides, and fatty acid glucamides;
- $C_8$ to $C_{22}$ alkyl mono- and oligoglycosides and their ethoxylated analogs, degrees of oligomerization from 1.1 to 5, in particular 1.2 to 2.0, and glucose as the sugar component, being preferred;
- mixtures of alkyl(oligo)glucosides and fatty alcohols, for example the commercially available product Montanov® 68;
- addition products of 5 to 60 mol ethylene oxide with castor oil and hardened castor oil;
- partial esters of polyols having 3 to 6 carbon atoms with saturated fatty acids having 8 to 22 carbon atoms;
- Sterols. "Sterols" are understood as a group of steroids that carry a hydroxyl group on the third carbon atom of the steroid structure and are isolated both from animal tissue (zoosterols) and from vegetable fats (phytosterols). Examples of zoosterols are cholesterol and lanosterol. Examples of suitable phytosterols are ergosterol, stigmasterol, and sitosterol. Sterols called "mycosterols" are also isolated from fungi and yeasts.
- Phospholipids. These are understood as principally the glucose phospholipids, which are obtained e.g. as lecithins or phosphatidylcholines from, for example, egg yolk or plant seeds (e.g. soybeans).
- fatty acid esters of sugars and sugar alcohols, such as sorbitol;
- polyglycerols and polyglycerol derivatives such as, for example, polyglycerol poly-12-hydroxystearate (commercial product Dehymuls® PGPH).

linear and branched fatty acids having 8 to 30 carbon atoms, and their Na, K, ammonium, Ca, Mg, and Zn salts.

The emulsifiers are used preferably in quantities from 0.1 to 25 wt %, in particular 0.5 to 15 wt %, based on the respective entire composition.

Nonionogenic emulsifiers having an HLB value from 8 to 18, according to the definitions set forth in the Römpp-Lexikon Chemie [Römpp chemical dictionary] (J. Falbe, M. Regitz, eds.), 10th edition, Georg Thieme Verlag Stuttgart, New York (1997), page 1764, are preferred. Nonionogenic emulsifiers having an HLB value from 10 to 16 are particularly preferred according to the present invention.

If the agents according to the present invention are hair coloring agents, they furthermore contain at least one oxidizing dye precursor product and/or at least one direct-absorbing dye. The known developer components, which can be used if applicable in combination with at least one coupler component, are suitable as an oxidizing dye precursor product.

Direct-absorbing dyes are usually nitrophenylenediamines, nitroaminophenols, azo dyes, anthraquinones, or indophenols. Preferred direct-absorbing dyes are the compounds known under the international designations or trade names HC Yellow 2, HC Yellow 4, HC Yellow 5, HC Yellow 6, HC Yellow 12, Acid Yellow 1, Acid Yellow 10, Acid Yellow 23, Acid Yellow 36, HC Orange 1, Disperse Orange 3, Acid Orange 7, HC Red 1, HC Red 3, HC Red 10, HC Red 11, HC Red 13, Acid Red 33, Acid Red 52, HC Red BN, Pigment Red 57:1, HC Blue 2, HC Blue 11, HC Blue 12, Disperse Blue 3, Acid Blue 7, Acid Green 50, HC Violet 1, Disperse Violet 1, Disperse Violet 4, Acid Violet 43, Disperse Black 9, Acid Black 1, and Acid Black 52, as well as 1,4-diamino-2-nitrobenzene, 2-amino-4-nitrophenol, 1,4-bis-(β-hydroxyethyl)amino-2-nitrobenzene, 3-nitro-4-(β-hydroxyethyl) aminophenol, 2-(2'-hydroxyethyl)amino-4,6-dinitrophenol, 1-(2'-hydroxyethyl)amino-4-methyl-2-nitrobenzene, 1-amino-4-(2'-hydroxyethyl)amino-5-chloro-2-nitrobenzene, 4-amino-3-nitrophenol, 1-(2'-ureidoethyl)amino-4-nitrobenzene, 4-amino-2-nitrodiphenylamine-2'-carboxylic acid, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid, and 2-chloro-6-ethylamino-1-hydroxy-4-nitrobenzene.

Cationic direct-absorbing dyes are preferably used. Particularly preferred in this context are:

(d) cationic triphenylmethane dyes such as, for example, Basic Blue 7, Basic Blue 26, Basic Violet 2, and Basic Violet 14;

(e) aromatic systems that are substituted with a quaternary nitrogen group, such as, for example, Basic Yellow 57, Basic Red 76, Basic Blue 99, Basic Brown 16, and Basic Brown 17; and (f) direct-absorbing dyes that contain a heterocycle which comprises at least one quaternary nitrogen atom, as recited, for example, in Claims 6 to 11 in EP-A2-998 908, to which reference is explicitly made at this juncture.

Preferred cationic direct-absorbing dyes of group (c) are, in particular, the following compounds:

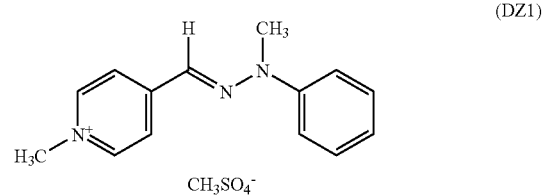
(DZ1)

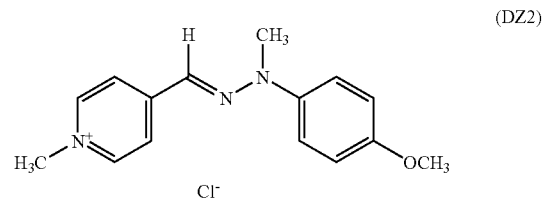
(DZ2)

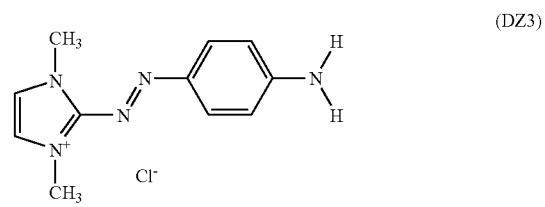
(DZ3)

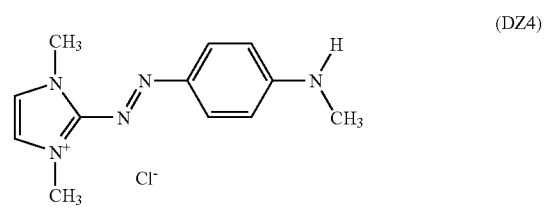
(DZ4)

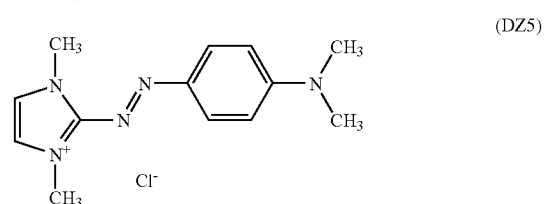
(DZ5)

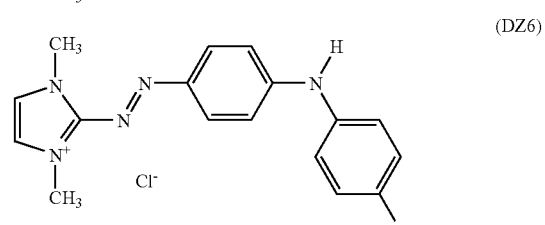
(DZ6)

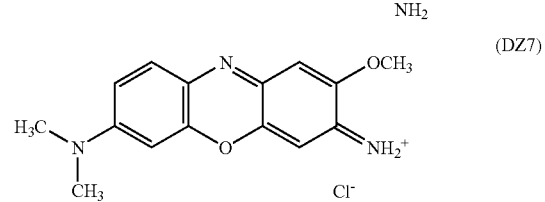
(DZ7)

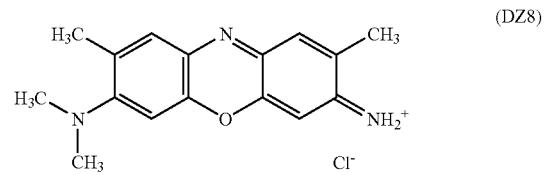
(DZ8)

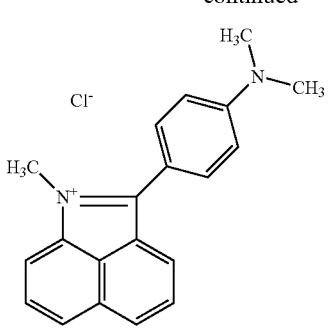 (DZ9)

The compounds of formulas (DZ1), (DZ3), and (DZ5), which are also known under the designations Basic Yellow 87, Basic Orange 31, and Basic Red 51, are very particularly preferred cationic direct-absorbing dyes of group (c).

The cationic direct-absorbing dyes that are marketed under the trademark Arianor® are, according to the present invention, likewise very particularly preferred cationic direct-absorbing dyes.

The agents according to the present invention in accordance with this embodiment contain the direct-absorbing dyes preferably in a quantity of 0.001 to 20 wt %, based on the entire agent.

In addition, the agents according to the present invention can also contain dyes occurring in nature, for example such as those contained in henna red, henna neutral, henna black, chamomile blossom, sandalwood, black tea, buckthorn bark, salvia, logwood, madder root, catechu, Spanish cedar, and alkanna root.

It is not necessary for the direct-absorbing dyes to represent homogeneous compounds in each case. The agents according to the present invention can instead, depending on the production methods for the individual dyes, also contain further components in subordinate quantities, provided they do not disadvantageously influence the styling result or do not have to be excluded for other (e.g. toxicological) reasons.

In addition to the aforesaid components, the agents can also contain all active substances, additives, and adjuvants known for corresponding cosmetic agents.

Further active substances, adjuvants, and additives are, for example:
- thickening agents such as agar-agar, guar gum, alginates, xanthan gum, gum arabic, karaya gum, locust bean flour, linseed gums, dextrans, cellulose derivatives, e.g. methyl cellulose, hydroxyalkyl cellulose, and carboxymethyl cellulose, starch fractions and derivatives such as amylose, amylopectin, and dextrins, clays such as, for example, bentonite, entirely synthetic hydrocolloids such as, for example, poly(vinylalcohol), and crosslinked polyacrylates if applicable;
- structuring agents such as maleic acid and lactic acid;
- perfume oils, dimethylisosorbide, and cyclodextrins;
- solvents and solubilizers such as ethanol, isopropanol, ethylene glycol, propylene glycol, glycerol, and diethylene glycol;
- quaternized amines such as methyl-1-alkylamidoethyl-2-alkylimidazolinium methosulfate;
- defoamers such as silicones;
- dyes for coloring the agent;
- anti-dandruff ingredients such as piroctone olamine, zinc omadine, and climbazole;
- substances for adjusting pH, such as, for example, usual acids, in particular edible acids, and bases;
- cholesterol;
- consistency agents such as sugar esters, polyol esters, or polyolalkyl ethers;
- fats and waxes such as spermaceti, beeswax, montan wax, and paraffins;
- fatty acid alkanolamides;
- complexing agents such as EDTA, NTA, β-alaninediacetic acid, and phosphonic acids;
- swelling and penetrating substances, such as glycerol, propylene glycol monoethyl ether, carbonates, hydrogencarbonates, guanidines, ureas, and primary, secondary, and tertiary phosphates;
- opacifiers such as styrene/PVP and styrene/acrylamide copolymers;
- pearlescent agents such as ethylene glycol mono- and distearate, as well as PEG-3 distearate;
- preservatives;
- stabilizing agents for hydrogen peroxide and other oxidizing agents;
- propellants such as propane-butane mixtures, $N_2O$, dimethyl ether, $CO_2$, and air;
- antioxidants.

With regard to further optional components as well as the quantities of those components that are used, reference is made expressly to the relevant manuals known to those skilled in the art.

The agents according to the present invention can be formulated in any form usual for cosmetic agents, for example in the form of solutions that can be applied onto the skin or hair as a face or hair lotion or as a pump or aerosol spray, in the form of creams, emulsions, waxes, gels, or also surfactant-containing foaming solutions or other preparations that are suitable for application to the skin or hair.

The agents according to the present invention are, however, by preference agents for the temporary deformation of keratinic fibers, i.e. styling agents. Preferred styling agents are styling gels, pump hair sprays, aerosol hair spray, pump hair foams, and aerosol hair foams.

"Hair foams" are understood as compositions that form a foam upon removal from a suitable container. It may be necessary to add to the agents ingredients that promote foam formation or that stabilize foam once it has been formed. Surfactants and/or emulsifiers, as already described above, are particularly suitable for this. Surfactants from the group of the cationic surfactants are used by preference.

Hair creams and hair gels generally contain structuring agents and/or thickening polymers which serve to impart the desired consistency to the products. Structuring agents and/or thickening polymers are used typically in a quantity from 0.1 to 10 wt %, based on the entire product. Quantities from 0.5 to 5 wt %, in particular 0.5 to 3 wt %, are preferred. Because the polymer combination used according to the present invention has self-thickening properties, however, the addition of further structuring agents and/or thickening polymers is not absolutely necessary. By preference, the agents according to the present invention contain no further structuring agents and/or thickening polymers.

If the agents according to the present invention involve an aerosol product, the latter mandatorily contains a propellant.

Propellants suitable according to the present invention are, for example, $N_2O$, dimethyl ether, $CO_2$, air, and alkanes having 3 to 5 carbon atoms, such as propane, n-butane, isobutane, n-pentane, and isopentane, and mixtures thereof. Dimethyl ether, propane, n-butane, isobutanes, and mixtures thereof are preferred.

The aforesaid alkanes, mixtures of the aforesaid alkanes, or mixtures of the aforesaid alkanes with dimethyl ether are preferably used as the only propellant. The invention also expressly encompasses, however, the concurrent use of propellants of the chlorofluorocarbon type, but in particular the fluorocarbons.

For a given spray apparatus, the size of the aerosol droplets or foam bubbles, and the respective size distribution, can be adjusted by way of the quantitative ratio between the propellant and the other constituents of the preparations.

The quantity of propellant used varies as a function of the specific composition of the agent, the packaging used, and the desired type of product (e.g. hair spray or hair foam). When conventional spray apparatuses are used, aerosol foam products contain the propellant preferably in quantities from 1 to 35 wt %, based on the entire product. Quantities from 2 to 30 wt %, in particular from 3 to 15 wt %, are particularly preferred. Aerosol sprays generally contain larger quantities of propellant. In this case the propellant is used preferably at a quantity from 30 to 98 wt %, based on the entire product. Quantities from 40 to 95 wt %, in particular from 50 to 95 wt %, are particularly preferred.

The aerosol products can be manufactured in usual fashion, As a rule all the constituents of the particular agent, with the exception of the propellant, are introduced into a suitable pressure-tight container. The latter is then sealed with a valve. Lastly, the desired quantity of propellant is introduced using conventional techniques.

A second subject of the invention is use of the agents according to the present invention for the temporary deformation of keratinic fibers.

The agents according to the present invention, and products that contain these agents, are notable in particular for the fact that they impart a very strong and humidity-resistant hairstyle hold to treated hair.

The deformation hold, also referred to as hairstyle hold, as well as the flexibility, elasticity, and plasticity, are determined for purposes of the present invention using the omega loop method.

For this, a dry hair strand (European Natural hair of the Kerling company, bonded dense tress, bonded at one end, total length 150 mm, free length 130 mm, width 10 mm, weight 0.9±0.1 g) is immersed for 30 seconds, as far as the upper edge of the adhesive bond, into the polymer solution to be investigated. The excess solution is then wiped off between the thumb and forefinger so that 0.5±0.02 g of solution remains on the hair. The hair strand, saturated with the solution to be investigated, is wound around a Teflon cylinder 36 mm in diameter, and the projecting ends are secured with a clip. The prepared strands are then dried and conditioned in an environmental chamber overnight at 25° C. and 50% relative humidity, or at 25° C. and 75% relative humidity.

The conditioned strand is carefully removed from the Teflon cylinder. The resulting omega loop—a ring-shaped structure of hair stabilized in shape by the polymer film that has formed—is clamped into the grippers mounted on the load cell and lowered to just above the baseplate of an AMETEK LF Plus universal testing instrument of AMETEK Precision Instruments Europe GmbH, Lloyd product group. The entire measurement is performed in an environmental chamber under constant climatic conditions, at 25° C. and 50% relative humidity or at 25° C. and 75% relative humidity.

In order to create standardized initial conditions, the measurement begins with application of a preload of 0.07 N at a rate of 30 mm min$^{-1}$. The omega loop is then compressed 8 mm at a rate of 60 mm min$^{-1}$, the force necessary therefor being measured. Once the characteristic force $F_1$ at the maximum deformation of 8 mm has been recorded, the strand is unloaded at 60 mm min$^{-1}$ until it has risen 10 mm from the baseplate. The next cycle begins from there, by once again applying the 0.07 N preload and then compressing the strand 8 mm; the applicable rates are the same as described above. Measurement of one omega loop encompasses a total of 10 cycles.

Four characteristic parameters for describing the mechanical properties of film-forming polymers can be determined using this measurement method. The hold, flexibility, plasticity, and elasticity can be calculated from the measured forces using the following formulas:

$$\text{Hold} = F_1 [N]$$

($F_1$ corresponds to maximum measurement force)

$$\text{Flexibility} = \frac{F_{10}}{F_1}$$

(indicates the ratio of maximum forces between the tenth and the first cycle)

$$\text{Plasticity} = \frac{2 \cdot H_1 - H_{10}}{H_1}$$

(where $H_1 = 9$ mm and $H_{10} = 9$ mm + permanent plastic deformation of the strand)

$$\text{Elasticity} = \frac{\dfrac{F_{10}(2\ \text{mm}) - F_{10}(1.5\ \text{mm})}{0.5}}{\dfrac{F_1(2\ \text{mm}) - F_{10}(1.5\ \text{mm})}{0.5}} = \frac{E_{10}}{E_1}$$

(to calculate the elasticity, the forces for a 1.5 mm and 2 mm deformation are acquired respectively from the first and the tenth cycle, and are correlated).

Humidity resistance can also be determined using the omega loop method. For this, hold is determined at 25° C. and 50% relative humidity, and at 25° C. and 75% relative humidity, and the results obtained are correlated. In general, hold decreases at higher relative humidity. The smaller the difference between hold at 25° C. and 50% relative humidity and at 25° C. and 75% relative humidity, i.e. the greater the ratio of hold at 25° C. and 50% relative humidity to hold at 25° C. and 75% relative humidity, the better the humidity resistance.

The Examples below are intended to explain the subject matter of the present invention without limiting it in any way.

EXAMPLES

The quantitative indications that follow are to be understood, unless otherwise indicated, as percentages by weight.

1 Styling Gels

Styling gels E1 to E5 according to the present invention were manufactured in accordance with the table below:

| Raw materials | E1 | E2 | E3 | E4 | E5 |
|---|---|---|---|---|---|
| PEG-40 Hydrogenated Castor Oil[1] | 0.40 | 0.40 | 0.40 | — | — |
| AMP-Ultra PC 1000[2] | 0.40 | 0.40 | 0.40 | 0.40 | 0.40 |
| Amphomer[3] | 2.50 | 2.50 | 2.50 | 2.50 | 2.50 |
| Diaformer Z 632N[4] | 2.50 | 6.25 | 7.50 | 6.25 | — |
| Diaformer Z 301N[5] | — | — | — | — | 6.25 |

-continued

| Raw materials | E1 | E2 | E3 | E4 | E5 |
|---|---|---|---|---|---|
| Perfume | 0.10 | 0.10 | 0.10 | 0.10 | 0.10 |
| Ethanol 96%, denatured | — | — | — | to make 100 | to make 100 |
| Water, deionized | to make 100 | to make 100 | to make 100 | — | — |

[1] Hydrogenated castor oil with approx. 40 to 45 EO units (INCI name: PEG-40 Hydrogenated Castor Oil) (BASF)
[2] 2-Amino-2-methylpropanol (INCI name: Aminomethyl Propanol) (Dow Chemical)
[3] INCI name: Octylacrylamide/Acrylates/Butylaminoethyl Methacrylate Copolymer (National Starch)
[4] Copolymer of stearyl acrylate, methacryloylethylamine oxide, and one or more monomers from among acrylic acid, methacrylic acid, and simple esters thereof (28 to 32 wt % solids in ethanol; INCI name: Acrylates/Stearyl Acrylate/Ethylamine Oxide Methacrylate Copolymer) (Clariant)
[5] Copolymer of methacryloylethylbetaine and two or more monomers from among methacrylic acid and simple esters thereof (28 to 32 wt % solids in ethanol; INCI name: Methacryloyl Ethyl Betaine/Acrylates Copolymer) (Clariant)

Even without the addition of usual thickening or structuring agents, ordinary mixing of the raw materials recited in the table yields water- or ethanol-based styling agents that exhibit the desired gel form and possess an outstanding degree of hold.

In addition, styling gels E6 to E12 according to the present invention were manufactured in accordance with the table below:

Examples E6 to E12 contain a number of further ingredients, in particular UV protection substances, further setting and/or thickening polymers, and perfume components, and show that such ingredients can be incorporated without difficulty into the agents according to the present invention.

2 Hair Sprays

Agents E13 to E14 according to the present invention were manufactured in accordance with the table below:

| Raw materials | E13 | E14 |
|---|---|---|
| AMP-Ultra PC 1000[2] | 0.9 | 0.2 |
| Amphomer[3] | 1.5 | 1.0 |
| Diaformer Z 632N[4] | 3.7 | 3.7 |
| Perfume | 0.1 | 0.1 |
| Water, deionized | 6.3 | 6.3 |
| Ethanol 96%, denatured | to make 100 | to make 100 |

In order to manufacture hair sprays, the agents were each introduced into a suitable pressure-tight container, which was then sealed with a valve. The propellant dimethyl ether was then added to each of the agents. The weight ratio of agent to dimethyl ether was 40:60 in each case.

| Raw materials | E6 | E7 | E8 | E9 | E10 | E11 | E12 |
|---|---|---|---|---|---|---|---|
| PEG-40 Hydrogenated Castor Oil[1] | — | — | 0.40 | 0.40 | 0.40 | 0.30 | 0.40 |
| AMP-Ultra PC 1000[2] | 0.75 | 0.66 | 0.40 | 0.40 | 0.40 | 0.40 | 0.40 |
| Amphomer[3] | 2.50 | 2.50 | 2.50 | 2.50 | 2.50 | 2.50 | 2.50 |
| Diaformer Z 632N[4] | 6.25 | 6.25 | 6.25 | 6.25 | 6.25 | — | 6.25 |
| Diaformer Z 301N[5] | — | — | — | — | — | 6.25 | — |
| Benzophenone-4[6] | 0.005 | — | 0.10 | 0.10 | 0.10 | 0.10 | 0.10 |
| Synthalen K[7] | 0.10 | — | — | — | — | — | — |
| Amaze XT[8] | — | 0.10 | — | — | — | — | — |
| Aculyn 22[9] | — | — | — | — | 2.00 | — | — |
| Aculyn 28[10] | — | — | — | 5.00 | — | — | — |
| Aculyn 44[11] | — | — | 3.50 | — | — | — | — |
| Dekafald[12] | — | — | — | — | 0.10 | 0.10 | 0.10 |
| Jaguar HP 105[13] | — | — | — | — | — | 1.00 | — |
| Tylose H 100000 YP2[14] | — | — | — | — | — | — | 1.50 |
| D-panthenol, 75% | — | — | 0.20 | 0.20 | 0.20 | 0.20 | 0.20 |
| Phenoxyethanol | — | — | 0.20 | 0.20 | 0.50 | 0.50 | 0.50 |
| Perfume | — | 0.10 | 0.20 | 0.20 | 0.20 | 0.10 | 0.20 |
| Ethanol 96%, denatured | — | — | 10 | 10 | 5 | — | 5 |
| Water, deionized | to make 100 | to make 100 | to make 100 | to make 100 | to make 100 | to make 100 | to make 100 |

[6] 2-Hydroxy-4-methoxybenzophenone-5-sulfonic acid
[7] Polyacrylic acid (approx. 89% active substance content; INCI name: Carbomer) (3V Sigma)
[8] Dehydrated xanthan gum (INCI name: Dehydroxyxanthan Gum) (National Starch)
[9] Copolymer of (meth)acrylic acid, (meth)acrylic acid ester, and Steareth-20-methacrylic acid ester (29.5 to 30.5 wt % solids in water; INCI name: Acrylates/Stereath-20 Methacrylate Copolymer) (Rohm and Haas)
[10] Copolymer of (meth)acrylic acid, (meth)acrylic acid ester, and Beheneth-25-methacrylic acid ester (19 to 21 wt % solids in water; INCI name: Acrylates/Beheneth-25 Methacrylate Copolymer) (Rohm and Haas)
[11] Polyethylene glycol with approx. 150 ethylene oxide units, modified with decyl alcohol and saturated methylenediphenyl diisocyanate monomers (34 to 36 wt % solids in propylene glycol/water (60:40); INCI name: PEG-150/Decyl Alcohol/SMDI Copolymer) (Rohm and Haas)
[12] 1,3-Dihydroxymethyl-5,5-dimethyhydantoin (approx. 54 to 56 wt % active substance in water; INCI name: DMDM Hydantoin) (Jan Dekker)
[13] Propylene glycol ether of guar gum (powder with approx. 3.5 to 10% moisture content; INCI name: Hydroxypropyl Guar) (Rhodia)
[14] Modified cellulose (90% active substance content; INCI name: Hydroxyethylcellulose) (Shin Etsu)

Agents E15 to E16 according to the present invention were also manufactured in accordance with the table below:

| Raw materials | E15 | E16 |
|---|---|---|
| AMP-Ultra PC 1000[2] | 1.3 | 1.0 |
| Amphomer[3] | 6.8 | 5.0 |
| Benzophenone-4[6] | 0.4 | 0.4 |
| Diaformer Z 712N[15] | 8.0 | 5.7 |
| Perfume | 0.2 | 0.3 |
| Water, deionized | 9.4 | 9.2 |
| Ethanol 96%, denatured | to make 100 | to make 100 |

[15]Copolymer of lauryl acrylate, stearyl acrylate, methacryloylethylamine oxide, and one or more monomers from among acrylic acid, methacrylic acid, and simple esters thereof (38 to 42 wt % solids in ethanol; INCI name: Acrylates/Lauryl Acrylate/Stearyl Acrylate/Ethylamine Oxide Methacrylate Copolymer) (Clariant)

In order to manufacture hair sprays, the agents were each introduced into a suitable pressure-tight container, which was then sealed with a valve. The propellant dimethyl ether was then added to each of the agents. The weight ratio of agent to dimethyl ether was 50:50 in these instances.

As compared with hair sprays based on the Amphomer film-forming polymer but that contain no additional polymer of the Diaformer type, these hair sprays according to the present invention are notable in particular for improved curl retention at high humidity, and improved humidity and perspiration resistance.

3 Foam Setting Agents

Agents E17 to E19 according to the present invention were manufactured in accordance with the table below:

| Raw materials | E17 | E18 | E19 |
|---|---|---|---|
| PEG-40 Hydrogenated Castor Oil[1] | 1.00 | 1.00 | 1.00 |
| AMP-Ultra PC 1000[2] | 0.35 | 0.35 | 0.35 |
| Amphomer[3] | 1.30 | 1.30 | 1.30 |
| Diaformer Z 632N[4] | 3.30 | — | 2.00 |
| Diaformer Z 651[16] | — | 3.30 | 1.50 |
| Lactic acid, 80% | 0.30 | 0.30 | 0.30 |
| Sodium benzoate | 0.30 | 0.30 | 0.30 |
| Natrosol 250 HHR[17] | 0.10 | 0.10 | 0.10 |
| Dow Corning 939[18] | 0.45 | 0.45 | 0.45 |
| Genamin CTAC[19] | 1.10 | 1.10 | 1.10 |
| Perfume | 0.15 | 0.15 | 0.15 |
| Water, deionized | to make 100 | to make 100 | to make 100 |

[16]Copolymer of lauryl acrylate, stearyl acrylate, methacryloylethylamine oxide, and one or more monomers from among acrylic acid, methacrylic acid, and simple esters thereof (28 to 32 wt % solids in ethanol/water (85:15); INCI name: Acrylates/Lauryl Acrylate/Stearyl Acrylate/Ethylamine Oxide Methacrylate Copolymer) (Clariant)
[17]Hydroxyethyl cellulose (INCI name: Hydroxyethylcellulose) (Hercules)
[18]Approx. 32 to 36% solids; INCI name: Amodimethicone, Trideceth-12, Cetrimonium Chloride (Dow Corning)
[19]Trimethylhexadecylammonium chloride (approx. 28 to 30% active substance in water; INCI name: Cetrimonium Chloride) (Clariant)

In order to manufacture aerosol hair foams, the agents were each introduced into a suitable pressure-tight container, which was then sealed with a valve. A propellant mixture made up of n-propane, n-butane, and isobutane (48/49/3) was then added to each of the agents. The weight ratio of agent to propellant mixture was 92:8 in each case.

4 Toning Foams

Agents E20 to E23 according to the present invention were manufactured in accordance with the table below:

| Raw materials | E20 | E21 | E22 | E23 |
|---|---|---|---|---|
| PEG-40 Hydrogenated Castor Oil[1] | 0.20 | 0.20 | 0.20 | 0.20 |
| AMP-Ultra PC 1000[2] | 0.35 | 0.35 | 0.35 | 0.35 |
| Amphomer[3] | 1.30 | 1.30 | 1.30 | 1.30 |
| Diaformer Z 632N[4] | 3.50 | 3.50 | — | 2.00 |
| Diaformer Z 651[16] | — | — | 3.50 | 1.50 |
| Citric acid monohydrate | 0.01 | 0.01 | 0.01 | 0.01 |
| Sodium benzoate | 0.30 | 0.30 | 0.30 | 0.30 |
| Natrosol 250 HHR[17] | 0.10 | 0.10 | 0.10 | 0.10 |
| D-panthenol 75% | 0.20 | 0.20 | 0.20 | 0.20 |
| Genamin CTAC[19] | 1.00 | 1.00 | 1.00 | 1.00 |
| Perfume | 0.10 | 0.10 | 0.10 | 0.10 |
| Basic Yellow 87 | 0.05 | 0.01 | 0.05 | 0.10 |
| Basic Orange 31 | 0.005 | — | 0.005 | — |
| Basic Red 51 | 0.005 | — | 0.005 | — |
| Basic Blue 99 | 0.10 | 0.02 | 0.10 | 0.20 |
| Basic Brown 16 | — | 0.01 | — | 0.02 |
| Water, deionized | to make 100 | to make 100 | to make 100 | to make 100 |

In order to manufacture aerosol toning foams, the agents were each introduced into a suitable pressure-tight container, which was then sealed with a valve. A propellant mixture made up of n-propane, n-butane, and isobutane (48/49/3) was then added to each of the agents. The weight ratio of agent to propellant mixture was 90:10 in each case.

5 Shampoos

Agents E24 to E26 according to the present invention were manufactured in accordance with the table below:

| Raw materials | E24 | E25 | E26 |
|---|---|---|---|
| Texapon NSO[20] | 40.00 | 40.00 | 40.00 |
| Dehyton G[21] | 6.00 | 6.00 | 6.00 |
| Cetiol HE[22] | 2.00 | 2.00 | 2.00 |
| AMP-Ultra PC 1000[2] | 0.20 | 0.20 | 0.25 |
| Amphomer[3] | 0.75 | 0.75 | 0.90 |
| Diaformer Z 632N[4] | 1.50 | — | 1.00 |
| Diaformer Z 651[16] | — | 1.50 | 0.60 |
| Citric acid monohydrate | 0.50 | 0.50 | 0.50 |
| Sodium benzoate | 0.50 | 0.50 | 0.50 |
| Perfume | 0.40 | 0.40 | 0.40 |
| Water, deionized | to make 100 | to make 100 | to make 100 |

[20]Lauryl ether sulfate, sodium salt (approx. 27.5% active substance; INCI name: Sodium Laureth Sulfate) (Cognis)
[21]N(2-hydroxyethyl)-N(cocamidoethyl)carboxymethyl glycinate sodium salt (approx. 39 to 31% active substance content; INCI name: Aqua (Water), Disodium Cocoamphodiacetate) (Cognis)
[22]Cocomonoglyceride with approx. 7.3 EO units (INCI name: PEG-7 Glyceryl Cocoate) (Cognis)

The agents were obtained in known fashion by mixing the raw materials recited in the table.

6 Demonstration of Action

The hold, flexibility, and humidity resistance of various polymer solutions were determined using the omega loop method (50% and 75% relative humidity, 25° C.). The first to be investigated were polymer solutions P1 and P2 and, as polymer solution P3, a mixture of solutions P1 and P2 at a 1:1 weight ratio The polymer solutions P1, P2, and P3 that were investigated each contained 5 wt % polymer.

| Raw materials | P1 | P2 |
|---|---|---|
| AMP-Ultra PC 1000[2] | 0.82 | — |
| Amphomer[3] | 5.00 | — |
| Diaformer Z 632N[4] | — | 16.70 |
| Water, deionized | to make 100 | to make 100 |

The results obtained, and the theoretically expected values for polymer solution P3 ("P3 (theory)"), are reproduced in the table below:

|  | P1 | P2 | P3 | P3 (theory) |
|---|---|---|---|---|
| Hold (cN) (50% R.H.) | 107 | 296 | 205 | 201.5 |
| Hold (cN) (75% R.H.) | 90 | 143 | 161 | 116.5 |
| Flexibility (%) (75% R.H.) | 72 | 86 | 100 | 79 |
| Humidity resistance (%) (Hold at 75%/50% R.H.) | 84 | 48 | 78 | 66 |

A comparison of the theoretical values ascertained by calculation for polymer solution P3 with the measurement results obtained shows clearly that the combination of copolymer A and amphoteric polymer B results, at high relative humidity, in a synergistic increase in hold and simultaneously in flexibility.

The invention claimed is:

1. A hair cosmetic agent comprising, in a cosmetically acceptable carrier,
   (A) a copolymer A comprising at least two monomers A1 and A2, wherein
      (a) monomer A1 is selected from the group consisting of acrylic acid, methacrylic acid, acrylic acid methyl ester, methacrylic acid methyl ester, acrylic acid ethyl ester, methacrylic acid ethyl ester, acrylic acid propyl ester, methacrylic acid propyl ester, acrylic acid isopropyl ester, methacrylic acid isopropyl ester, acrylic acid stearyl ester and methacrylic acid stearyl ester; and
      (b) monomer A2 is (meth)acryloylethylamine oxide; and
   (B) at least N-octylacrylamide/acrylic acid/tert-butylaminoethyl methacrylate copolymer as a film-forming and/or -setting amphoteric polymer B.

2. The agent of claim 1, wherein the copolymer A comprises from 0.01 to 20 wt % of the agent.

3. The agent of claim 2, wherein the copolymer A comprises from 0.1 to 5 wt % of the agent.

4. The agent of claim 1, wherein the amphoteric polymer B comprises 0.01 to 20 wt % of the agent.

5. The agent of claim 4, wherein the amphoteric polymer B comprises 1.0 to 10 wt % of the agent.

6. The agent of claim 1, wherein the weight ratio of copolymer A to amphoteric polymer B is from 1:20 to 20:1.

7. The agent of claim 6, wherein the weight ratio of copolymer A to amphoteric polymer B is from 1:10 to 10:1.

8. The agent of claim 7, wherein the weight ratio of copolymer A to amphoteric polymer B is from 1:1 to 5:1.

9. The agent of claim 1 further comprising a silicone compound selected from the group consisting of silicone oils and silicone gums.

10. A method for temporarily deforming hair comprising contacting the hair with the composition of claim 1.

* * * * *